(12) United States Patent
Baek et al.

(10) Patent No.: US 7,241,011 B2
(45) Date of Patent: Jul. 10, 2007

(54) FUNDUS IMAGING SYSTEM

(75) Inventors: Seung-Ho Baek, Pittsford, NY (US); Douglass L. Blanding, Rochester, NY (US); Rongguang Liang, Penfield, NY (US); Dale L. Tucker, Rochester, NY (US); Jeffery R. Hawver, Marion, NY (US)

(73) Assignee: Carestream Health, Inc., Rochester, NY (US)

( * ) Notice: Subject to any disclaimer, the term of this patent is extended or adjusted under 35 U.S.C. 154(b) by 337 days.

(21) Appl. No.: 10/977,434

(22) Filed: Oct. 29, 2004

(65) Prior Publication Data

US 2006/0092376 A1   May 4, 2006

(51) Int. Cl.
*A61B 3/14* (2006.01)
(52) U.S. Cl. ............... 351/206; 351/207; 351/208; 351/209; 351/210; 351/220; 600/452; 606/4; 396/18
(58) Field of Classification Search ........ 351/206–210, 351/220; 600/452; 606/4; 396/18, 51
See application file for complete search history.

(56) References Cited

U.S. PATENT DOCUMENTS

| 4,838,680 | A | 6/1989 | Nunokawa |
| 5,572,266 | A | 11/1996 | Ohtsuka |
| 5,713,047 | A | 1/1998 | Kohayakawa |
| 5,943,116 | A | 8/1999 | Zeimer |
| 6,546,198 | B2 | 4/2003 | Ohtsuka |
| 6,636,696 | B2 | 10/2003 | Saito |
| 7,001,019 | B2 * | 2/2006 | Takagi et al. ............... 351/211 |

* cited by examiner

*Primary Examiner*—Hung Dang
*Assistant Examiner*—Joseph Martinez

(57) ABSTRACT

An apparatus (220) for obtaining a scanned image of an eye has a reference locator for pupil alignment apparatus along an optical axis. A pupil profiling apparatus for obtaining an outline of the pupil has a pupil profiling light source (176), a sensor (170) for detecting reflected light, and a control logic processor (104) for computing an outline of the pupil according to detected light. An illumination apparatus (112) for directing visible illumination into the eye has a spatial light modulator (125) for shaping an illumination beam according to the detected outline, a scanning element (229), and a camera (146) for obtaining the scanned image by sensing a portion of the reflected illumination.

37 Claims, 23 Drawing Sheets

FUNDUS IMAGING SYSTEM

CROSS REFERENCE TO RELATED APPLICATIONS

Reference is made to commonly-assigned copending U.S. patent application Ser. No. 10/947,018, filed Sep. 22, 2004, entitled FUNDUS CAMERA HAVING SCANNED ILLUMINATION AND PUPIL TRACKING by Liang et al.; the disclosure of which is incorporated herein.

FIELD OF THE INVENTION

This invention generally relates to electronic imaging apparatus for fundus imaging and more particularly relates to an improved fundus imaging apparatus for non-mydriatic imaging using scanned slit illumination and an electronically controlled aperture, with automated operator controls and compensation for patient movement.

BACKGROUND OF THE INVENTION

Fundus camera imaging is acknowledged to be an important diagnostic tool for detection of various conditions affecting the eye, including diabetic retinopathy and macular degeneration. Various embodiments of fundus imaging apparatus are disclosed, for example in U.S. Pat. No. 5,713,047 (Kohayakawa); U.S. Pat. No. 5,943,116 (Zeimer); U.S. Pat. No. 5,572,266 (Ohtsuka); U.S. Pat. No. 4,838,680 (Nunokawa); U.S. Pat. No. 6,546,198 (Ohtsuka); and U.S. Pat. No. 6,636,696 (Saito).

While these patents attest to continuous improvements in fundus camera design, there are still significant hurdles to widespread acceptance and usability of these devices. Among disadvantages noted with current devices are high cost and complexity, difficulty of operation, large size, and image quality limitations. These disadvantages hinder the successful deployment of fundus cameras in primary care physician (PCP) offices or in medical test labs, where they could be used by a technician having relatively little training in device operation and imaging, to obtain images that can be assessed by specialists at some other location or at some later time.

In order to effect simple operation, it would be advantageous for the fundus imaging apparatus to have an operator interface that provides capable controls for operation, with operator feedback as well as automated response to events such as patient head and eye movement. The fundus imaging apparatus should be comfortable for the patient and allow images to be taken efficiently within a short amount of time, without undue stress on the patient or complexity for the operator.

A further significant disadvantage of existing fundus imaging apparatus relates to the requirement for pupil dilation. For most patients, artificially induced enlargement of the pupil is necessary in order to allow sufficient light into the eye of the patient for fundus observation and image capture. At best, pupil dilation is uncomfortable and at least temporarily unsettling; at worst, dilation can even be dangerous for some individuals. Pupil dilation itself requires a chemical application that can only be administered under the care of someone who is suitably trained and certified. A number of commercially available fundus imaging systems claim to be "non-mydriatic", that is, operable without pupil dilation. However, in practice, pupil dilation is still often required when using these apparatus.

While it is known that, given a large population of individuals, there can be a range of pupil sizes and a variety of pupil shapes, conventional fundus imaging apparatus are not adaptable to individual eye geometries. Instead, in practice, averaged values are used for approximating pupil size with conventional fundus imaging equipment. Little attempt is made to adapt camera operation to suit the particular characteristics of each individual eye.

In particular, the illumination optics subsystem of conventional fundus imaging apparatus is designed in such a way that it requires pupil dilation for most patients. In order to provide a truly non-mydriatic fundus imaging system that renders pupil dilation unnecessary and that can be reliably used by relatively untrained personnel, improved design of the illumination system would be required. However, the efforts of designers and manufacturers of these devices have been directed to providing more sophisticated imaging and assessment functions, many of which may actually require dilation in all cases. Thus, the limitations due to illumination subsystem design have been largely ignored and dilation is generally accepted as a requirement. For this reason, it can be seen that there is a need for an improved fundus imaging apparatus having an illumination system that allows fully non-mydriatic retinal imaging for a broad range of patients and having a set of operations tools that support non-mydriatic imaging with minimum training requirements.

SUMMARY OF THE INVENTION

It is an object of the present invention to provide a fundus imaging apparatus that promotes non-mydriatic imaging. With this object in mind, the present invention provides an apparatus for obtaining a scanned image of the eye, comprising:

a) a reference locator for positioning a patient at a viewing position;

b) a pupil alignment apparatus for aligning the pupil of the eye along an optical axis;

c) a pupil profiling apparatus for obtaining an outline of the pupil using light outside the visible spectrum, comprising:
  i) a pupil profiling light source for illuminating the eye surface;
  ii) a sensor for detecting reflected light from the pupil profiling light source; and
  iii) a control logic processor in communication with the sensor for computing an outline of the pupil according to detected light;

d) an illumination apparatus for directing visible illumination into the eye, comprising:
  i) a spatial light modulator for shaping an illumination beam, in cross-section perpendicular to the beam direction, according to the detected outline of the pupil;
  ii) a scanning element for scanning at least one partition of the shaped illumination beam into the pupil; and e) a camera for obtaining the scanned image by sensing a portion of the illumination beam reflected from within the eye.

From another aspect, the present invention provides an apparatus for obtaining a scanned image of the eye, comprising:

a) an adjustable alignment section for aligning the pupil of the eye along an optical axis;

b) a first light source for illuminating the eye surface;

c) a sensor for detecting light from the first light source reflected from the eye and forming a first image of the eye surface;

d) a display for displaying the first image to an operator;

e) at least one pointing mechanism for providing a pupil-locating signal from the operator;

f) a control logic processor for detecting an outline of the pupil according to the first image from the sensor;

g) an illumination apparatus for shaping an illumination beam according to the detected outline of the pupil and for scanning a partition of the shaped illumination beam into the pupil; and h) a camera for obtaining the scanned image by sensing the illumination beam reflected from within the eye.

It is a feature of the present invention that it provides a fundus imaging apparatus that adapts to the dimensional characteristics of each patient's pupil, allowing the illumination beam to be custom-fitted to each eye being imaged.

It is an advantage of the present invention that it minimizes or eliminates the requirement for pupil dilation for fundus imaging.

It is a further advantage of the present invention that it provides the capability for full-color fundus imaging.

It is yet a further advantage of the present invention that it provides a fundus imaging system with a larger field of view than conventional systems.

It is yet a further advantage of the present invention that it allows straightforward operation by a non-specialist, without requiring extensive operator training.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

System Configuration

Figure 1:
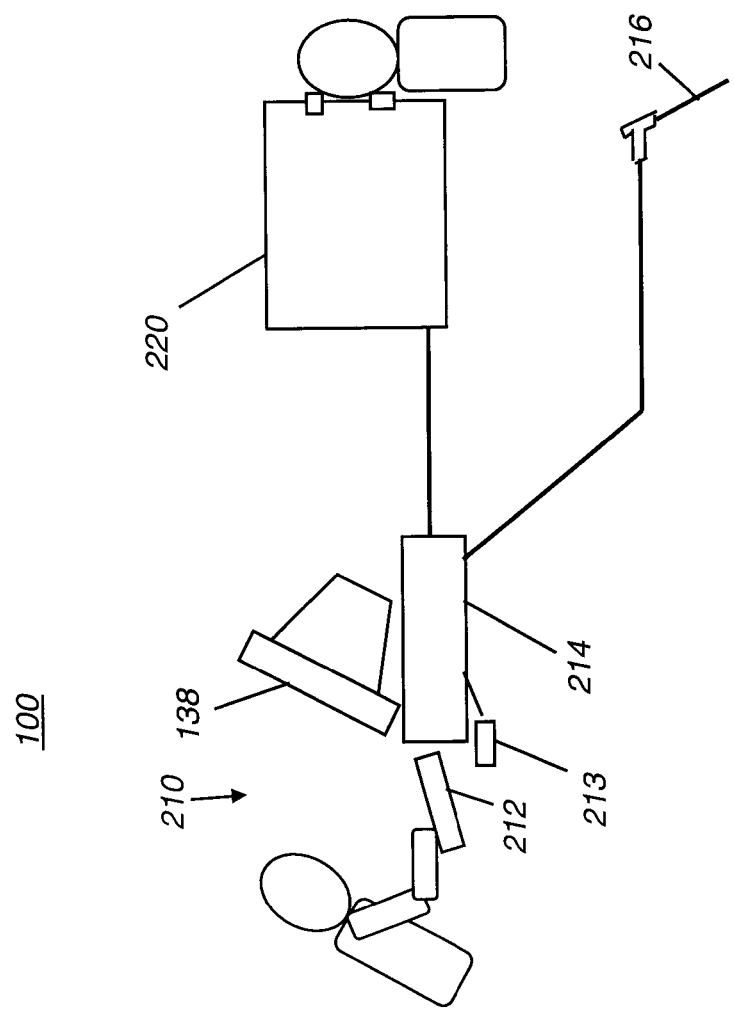
FIG. 1 is a schematic block diagram of the imaging system of the present invention.

Referring to FIG. 1, there is shown a fundus imaging system 100 according to the present invention. To support fundus imaging system 100, a control workstation 210 has a display 138, a keyboard 212, and a control logic processor 214 for providing control logic and operator interface functions. Imaging functions are provided by optical, electro-optical, and electronic components within a fundus imaging appliance 220. A network 216 allows communication between fundus imaging system 100 and processing and storage devices at other networked sites. Using network 216, for example, fundus images obtained by fundus imaging system 100 can be uploaded to other sites, such as to sites where diagnostic assessment is performed remotely. Alternately, software, instructions, or other data could be downloaded from other networked sites to fundus imaging system 100 or to control workstation 210.

There are a number of alternate embodiments possible based on the overall arrangement of FIG. 1. For example, the function of control logic processor 214 may be performed by logic components within fundus imaging appliance 220, rather than by a separately packaged processor, as shown in FIG. 1. Operator interface functions provided by display 138 and keyboard 212 could be combined in a touchscreen console, for example. The connection to network 216 may be a standard Ethernet connection, a dedicated network telecommunications connection, or a dial-up modem. In one embodiment, network 216 allows wireless connection. Alternately, the connection to network 216 may be dispensed with altogether, such that fundus imaging appliance 220 records fundus imaging data onto a data storage medium such as a removable storage medium, which could be as a magnetic, electronic, or optical storage medium, for example.

Conventional Illumination Arrangement

Figure 3:
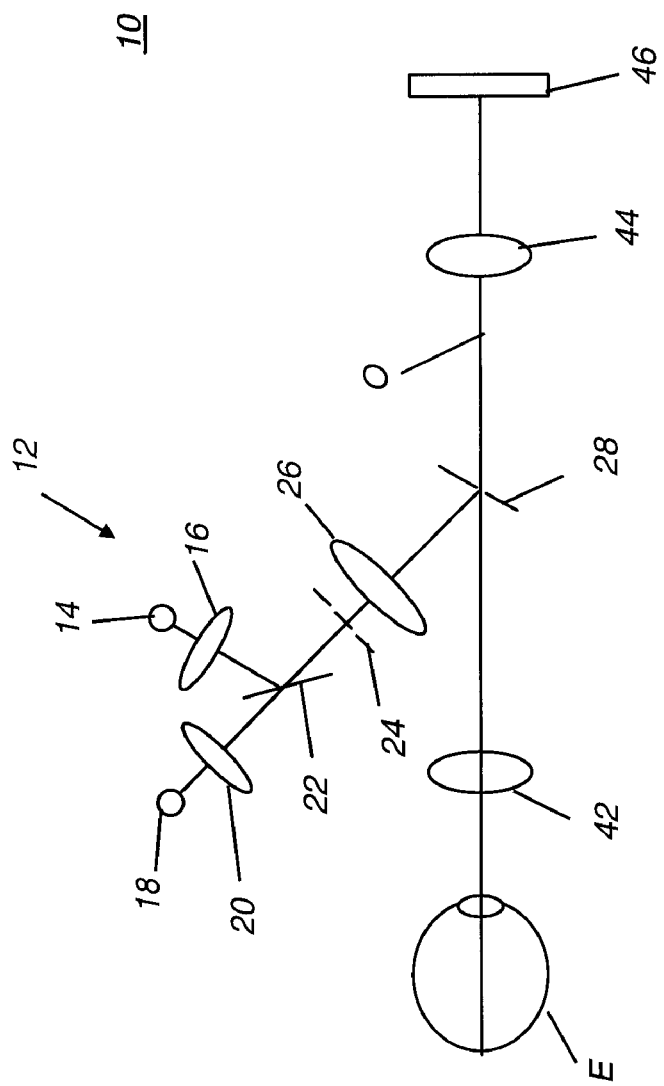
FIG. 3 is a schematic block diagram showing the overall arrangement of illumination apparatus components within a conventional fundus imaging apparatus.

In order to more fully appreciate the improved apparatus and method of the present invention, it is first instructive to review, at a high level, the operation of the illumination subsystem in a conventional fundus imaging 30 apparatus. Referring to FIG. 3, there is shown a fundus imaging apparatus 10 in which a conventional illumination section 12 is used. The patient's eye E is positioned along an optical axis O using an alignment subsystem, not shown in FIG. 3, but described subsequently. Illumination section 12 directs light either from an observation light source 14 and a lens 16 or from an image capture light source 18 and a lens 20 as controlled by control logic circuitry (not shown in FIG. 3). A half-mirror 22 directs light from the appropriate source through a ring-slit diaphragm 24 and a lens 26, to an apertured mirror 28. Apertured mirror 28 directs the illumination light along axis O and toward the pupil for illuminating the retina of eye E. Depending on the use of fundus imaging apparatus 10 at any one time, either observation light source 14 or image capture light source 18 are activated. Observation light source 14 is typically infrared (IR) light, to which eye E is insensitive. Image capture light source 18, on the other hand, may be a high-brightness source such as a xenon lamp, for example. Depending on the application, image capture light source 18 may be pulsed or strobed.

Figure 4:
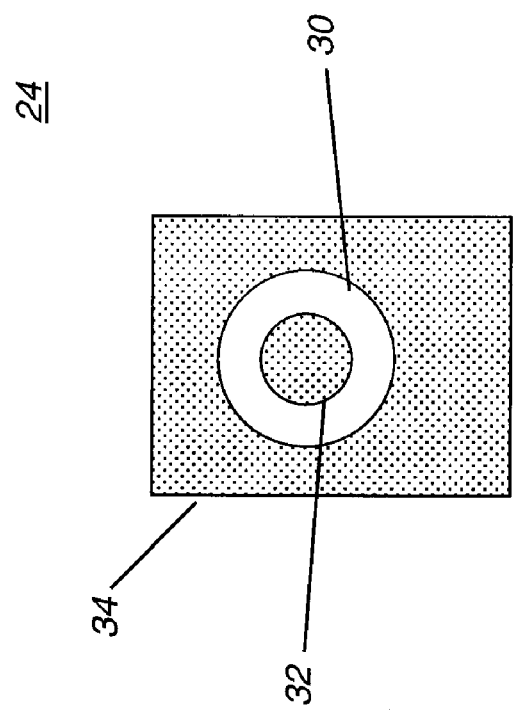
FIG. 4 is a plan view of a ring-slit diaphragm used in a conventional fundus imaging apparatus.

Ring-slit diaphragm 24 has the characteristic functional arrangement shown in FIG. 4. Light is transmitted through an inner ring 30 and is blocked at a middle section 32 and at an outer section 34. As is shown in the received illumination ring of FIG. 5, inner ring 30 is directed into a pupil 36 of the patient as a ring 40 of illumination. To obtain the retinal image, apertured mirror 28 (FIG. 3) has an aperture suitably centered about optical axis O to allow light that has been reflected from the retina of eye E and directed through lenses 42 and 44 to a sensor 46, such as a CCD.

The high-level block diagram of FIG. 3 thus gives an overview of illumination section 12 that applies for conventional fundus imaging apparatus. There have been numerous methods disclosed for optimizing the performance of illumination section 12, including components arranged to prevent stray reflected light from the cornea of eye E from being directed back toward sensor 46. However, the basic pattern of FIG. 3 is conventionally followed for these devices.

Figure 5:
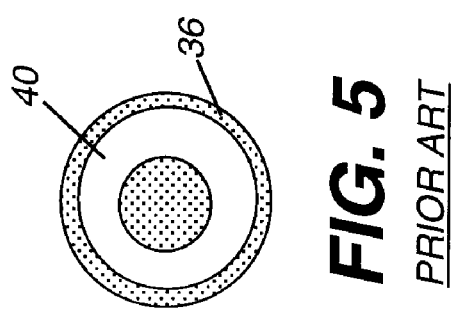
FIG. 5 is a plan view representation of the ring of illumination applied to the pupil of a patient in a conventional apparatus.

Among disadvantages of this conventional method is the relatively small field that is available. To compensate for this shortcoming, a series of tiled sections is typically imaged. In some cases, conventional image capture uses a narrow range of wavelengths, resulting in monochromatic images. The static ring 40 of illumination as shown in FIG. 5 is disadvantageous, since this ring occupies a portion of the image area during image capture. The combination of ring-slit diaphragm 24 and apertured mirror 28 acts to block scattered rays of illumination from the cornea, thereby obstructing these rays from affecting sensor 46. As yet another disadvantage, alignment of the patient's pupil with the conventional fundus imaging apparatus is time-consuming, since ring 40 must be aimed fully within the outline of the pupil and must avoid the iris.

Overview of Illumination Embodiments

The apparatus and method of the present invention eliminate the need for a separate ring of illumination as in conventional fundus imaging apparatus, shown as static ring 40 in FIG. 5. Instead, the apparatus and method of the present invention use one or more moving members to selectively partition the illumination beam from either observation light source 14 or image capture light source 18, directing one or more partitions or segments of the illumination beam to eye E and allowing light reflected from the retina of eye E to be detected at sensor 46, while also blocking reflected light from the cornea of eye E from sensing components.

Figure 6:
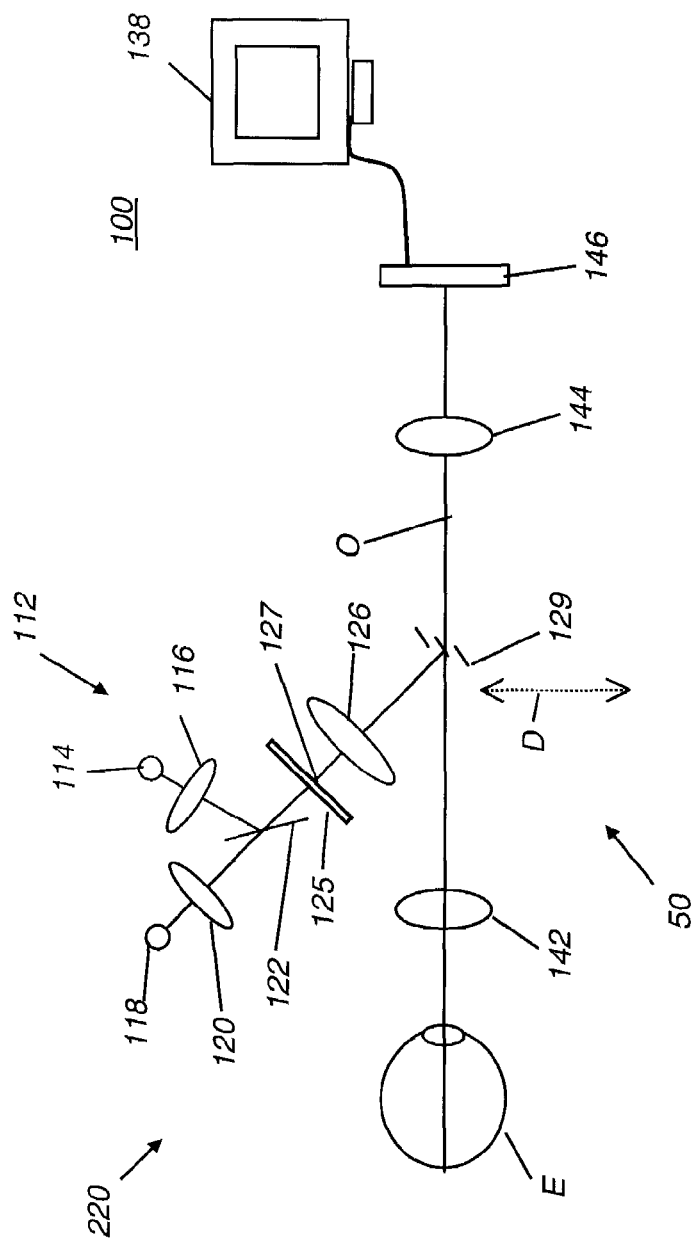
FIG. 6 is a schematic block diagram showing the overall arrangement of illumination apparatus components in a fundus imaging apparatus of the present invention.

Referring to FIG. 6, there is shown, in block diagram form, an overview of fundus imaging appliance 220 in fundus imaging system 100 of the present invention. Illumination section 112 directs light either from an observation light source 114 and a lens 116 or from an image capture light source 118 and a lens 120 as controlled by control logic circuitry (not shown in FIG. 6). A half-mirror 122 or, alternately, a dichroic surface, directs light from the appropriate source through a transmissive spatial light modulator 125 which, acting as a type of transmissive light valve, provides an electronically controlled aperture 127 for the illumination beam, shaping the illumination beam as described subsequently. The illumination beam is directed by a lens 126 to an illumination beam partitioning mechanism 50. Illumination beam partitioning mechanism 50 segments the illumination beam cross-sectionally, as is described subsequently. To do this, illumination beam partitioning mechanism 50 uses a reciprocating partitioning member 129 in the embodiment of FIG. 6. Reciprocating partitioning member 129 moves in a direction D and scans one or more segments of the illumination beam through a lens 142 and into the eye E. Reflected light from the retina of eye E is then passed through reciprocating partitioning member 129, with unwanted reflected light from the cornea blocked. The light reflected from the retina is thus directed through a lens 144 to a sensor 146. A display 138, such as a CRT or LCD monitor, is used in conjunction with sensor 146 and with cornea sensing camera or other sensing components, as described subsequently.

As the overview of FIG. 6 shows, illumination section 112 of the present invention directs the illumination beam from either observation light source 114 or image capture light source 118 toward the eye E and conditions the illumination beam in two ways:

(i) positioning and shaping the illumination beam through spatial light modulator 125; and (ii) partitioning the illumination beam at reciprocating partitioning member 129 into at least one illuminated segment that receives its corresponding partition of the illumination beam and at least one blocked segment that has its corresponding portion of the illumination beam blocked and, further, scanning the at least one illuminated segment along the field, thereby illuminating the complete field over time.

This dimensioning and conditioning of the illumination beam and method of scanning provide exceptional advantages for effecting a truly non-mydriatic illumination system for retinal imaging. It is worthwhile to observe that, while steps (i) and (ii) above are executed in this order in the embodiments described herein, a different order could be used, so that the illumination beam is first partitioned (step ii, above), then shaped (step i, above).

Shaping the Illumination Beam

The conventional ring-slit illumination method described with reference to FIGS. 3–5 directs a static ring 40 of illumination to the eye E being imaged. Among the problems inherent to this approach is its relatively poor adaptability to the dimensions of the pupil of eye E. Not only do pupils differ in diameter from one patient to the next, but the actual shape of the pupil itself can vary from circular shape. Dilated pupils for different patients, for example, can vary in diameter between about 6 and 8 mm. Conventional fundus imaging systems reach some compromise for variable pupil dimensions using methods such as a variety of selectable ring-slit diaphragms 24. For example, a set of different ring-slit diaphragms 24, or other apertured devices, can be provided on a selector wheel or other mechanism, allowing an operator to select the aperture that is best suited to the dimensions of the patient's pupils. Any aperture selected in the place of ring-slit diaphragm 24 is, at best, an approximation and must fit the illumination ring 40 within the outer dimensions of the pupil for best operation. Providing illumination that extends even slightly beyond the borders of the pupil of eye E is not optimal, since stray, diffused light from the surrounding iris of eye E can easily be directed back along optical axis O and degrade image quality obtained at sensor 46.

Figure 7:
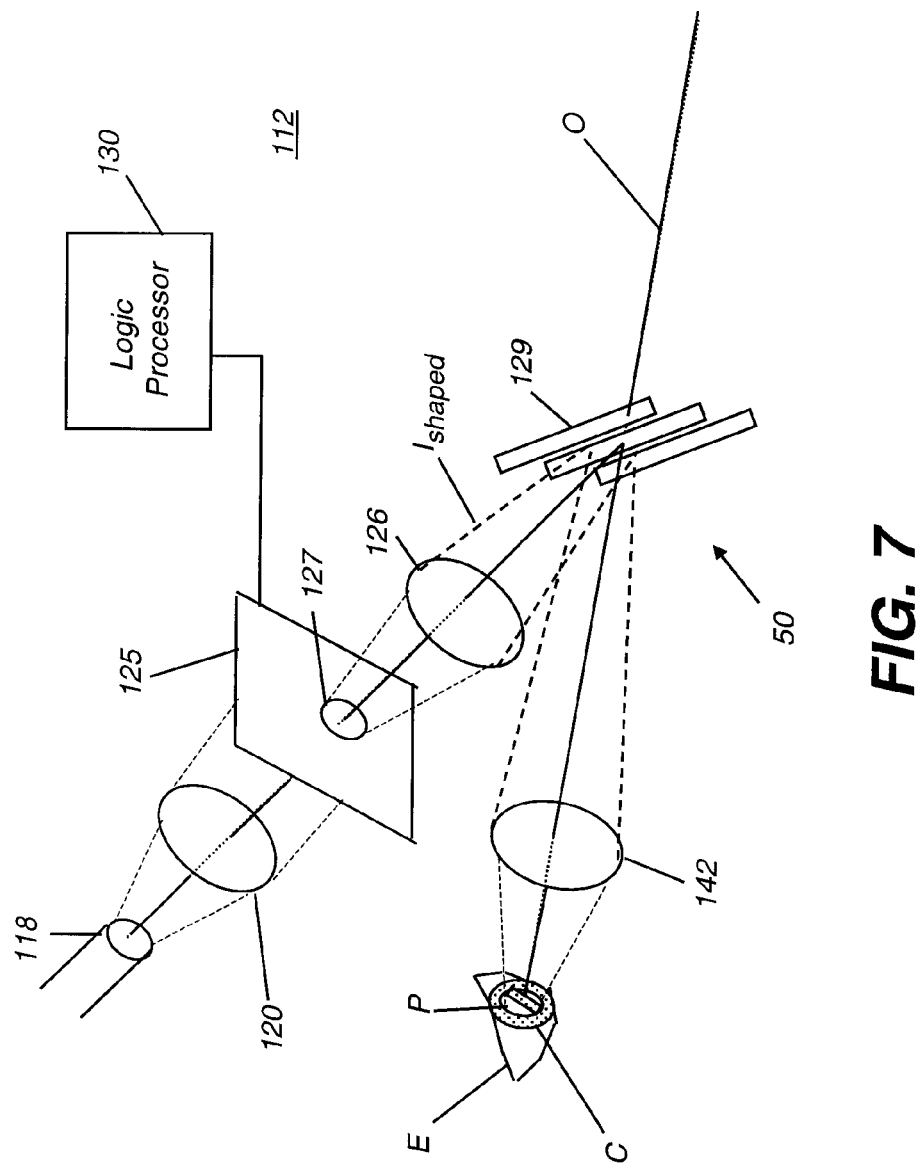
FIG. 7 is a perspective block diagram showing the beam shaping behavior of the illumination apparatus of the present invention.
Figure 8B:
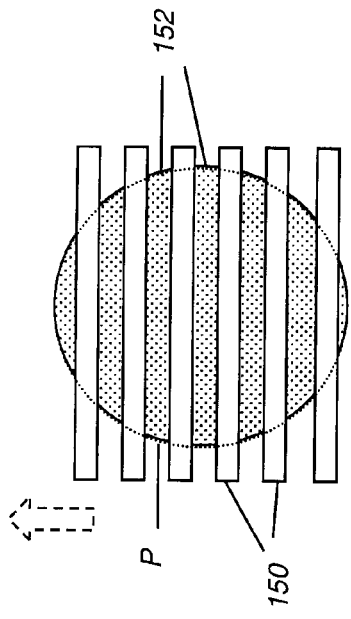
FIGS. 8A–8D are plan views showing the partition scanning used for illuminating the pupil using the apparatus and method of the present invention.
Figure 8D:
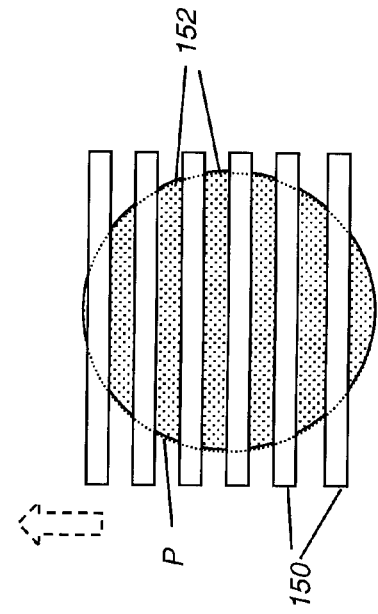
Figure 8A:
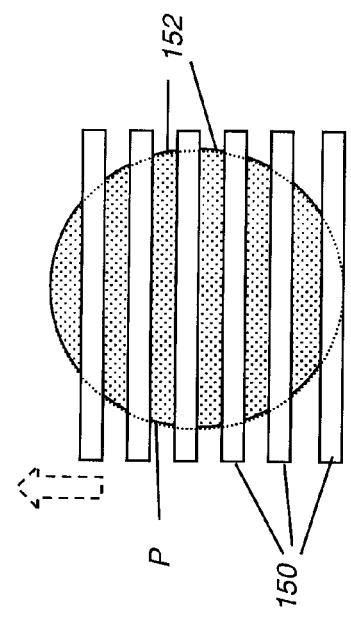
Figure 8C:
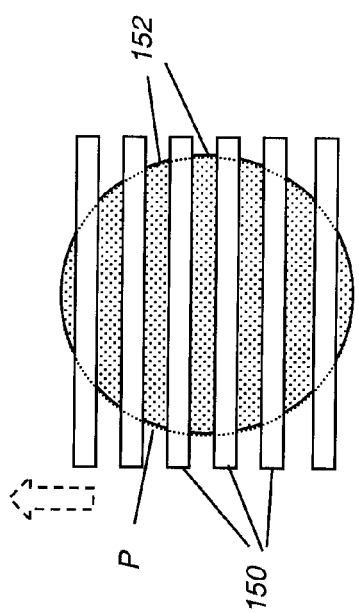

The apparatus and method of the present invention approach this problem in a different manner, by shaping the illumination beam according to the detected coordinates of the pupil. This method shapes the illumination beam, when considered in cross-sectional profile, to match dimensional profile of the pupil, in size, placement, and overall shape. Referring to FIG. 7, there is shown, in perspective view, the optical path of illumination to the pupil from image capture light source 118. It must be noted that the same beam shaping operation applies for light from either image capture light source 118 or observation light source 114 (FIG. 6). In FIG. 7, light from image capture light source 118 is directed through lens 120 toward spatial light modulator 125, which provides an electronically controlled aperture 127 that is sized to correspond to the outline of pupil P of eye E. Electronically controlled aperture 127 provides a mask for the illumination beam to form a shaped illumination beam $I_{shaped}$, which is directed through lens 126 and goes to illumination beam partitioning mechanism 50. Here, shaped illumination beam $I_{shaped}$, is segmented and reflected from reciprocating partioning member 129 or other component, then is directed through lens 142 to pupil P.

There are a number of ways to provide electronically controlled aperture 127 for conditioning the cross-sectional profile of the illumination beam. Spatial light modulator 125 may be a transmissive LCD, for example, such as an LCD spatial light modulator, blocking light from around electronically controlled aperture 127 in a masking pattern that corresponds to pupil P coordinates and dimensions. In this way, illumination can be directed to the full area of pupil P, but not extending outside the circumference of pupil P.

One advantage of using electronically controlled aperture 127 relates to light level adjustment. In its simplest embodiment, aperture 127 can be formed by setting pixels within the aperture fully on (represented by data level 255 in some imaging environments using 8-bit data representation, for example), or fully transparent to incident light; pixels outside electronically controlled aperture 127 would be fully off (represented by data level 000, for example), or fully opaque to incident light. However, intermediate values for light transmission are also available when using a spatial light modulator such as an LCD or digital micromirror device. Thus, it can be advantageous to dim the light in electronically controlled aperture 127 to less than the full brightness level. Using the exemplary data levels given above, for example, pixels within electronically controlled aperture 127 may not be fully on, at data level 255, but one or more of them may be partially on, at data level 219, for example. In this way, fine tuning adjustment of illumination intensity can also be achieved at spatial light modulator 125 using the apparatus of the present invention.

In one embodiment, the outline of pupil P is detected by an electronic camera or other sensor, as described subsequently. Image data from this camera is processed by a control logic processor 130, as shown in FIG. 7, to determine pupil P position and dimensional coordinates using pattern recognition and other imaging algorithms such as outline detection algorithms, employing methods familiar to those skilled in the imaging arts. Overall, the mechanism used as pupil sensor may have any of a number of components and may be fully automated or require operator interaction, such as for centering of sensor measurements or for verification of pupil outline and dimensions. This pupil sensing subsystem may also include feedback and adjustment mechanisms for pupil tracking, adapting to subtle changes in pupil position over time.

Figure 19:
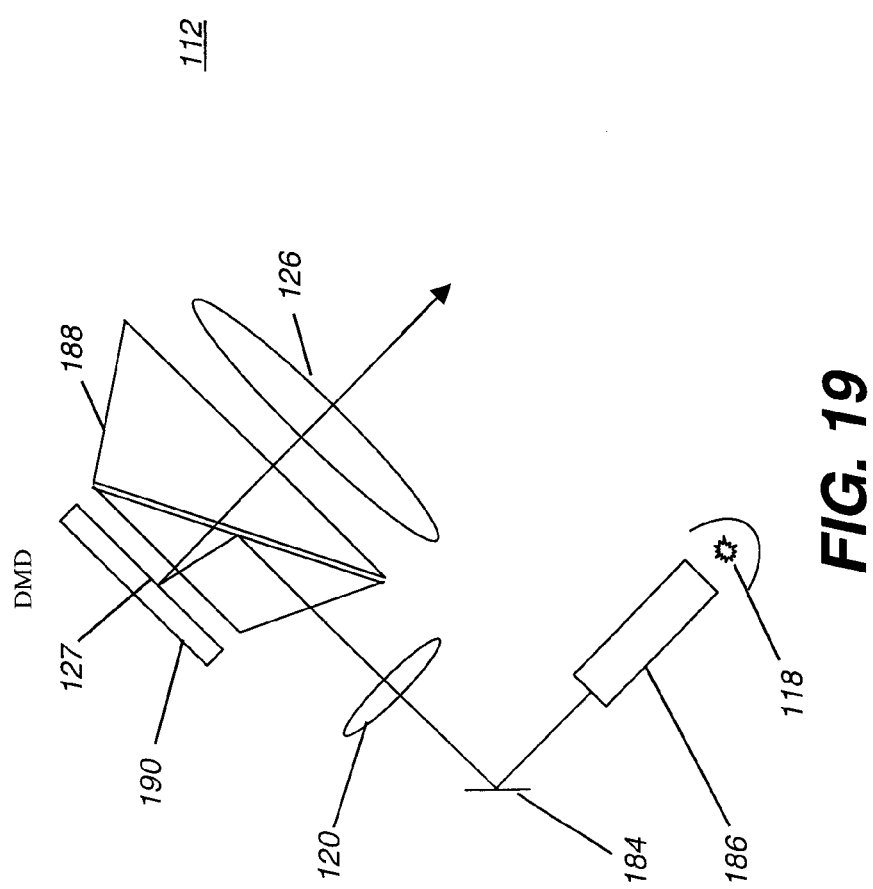
FIG. 19 is a block diagram showing an alternate embodiment for illumination components.

It must be noted that mechanisms other than transmissive spatial light modulators 125 could be used to provide electronically controlled aperture 127 for beam shaping. Reflective spatial light modulators and light valves could also be used for this purpose, as is shown in FIG. 19. Here, image capture light source 118 provides light that may be conditioned by a uniformizer 186 or other component and directed, by an optional mirror 184, through lens 120 and to a prism 188 or a beamsplitter of some type. Prism 188 directs the light toward a reflective light valve, such as a digital micromirror device 190 in the embodiment of FIG. 19. Digital micromirror device 190 then provides electronically controlled aperture 127, modulating the incident light to provide, through lens 126, an illumination beam that is shaped, in cross-sectional profile, according to data provided about the dimensions and position of the pupil. A similar arrangement to that of FIG. 19 would be used for a reflective LCD spatial light modulator used in place of digital micromirror device 190, with a polarization beamsplitter providing the light directing function of prism 188.

Partitioning the Illumination Beam

For obtaining an image, the full shaped illumination beam $I_{shaped}$ provided through spatial light modulator 125 in FIG. 7 cannot be provided to pupil P. If this were to happen, there would be excessive light reflection from the cornea C of eye E, resulting in unacceptably poor image quality. Instead, the present invention provides a cross-sectional partitioning or segmenting of the illumination beam. Referring to the sequence shown in FIGS. 8A–8D, the circular shape represents the two-dimensional shape of the patient's pupil P, to which the two-dimensional cross-section of the illumination beam, as shaped by illumination section 112, corresponds. As described with reference to FIGS. 6 and 7, the shape of P describes the cross-sectional "envelope" of the illumination beam, as modulated through spatial light modulator 125 or other device that provides electronically controlled aperture 127. Reciprocating partitioning member 129 of FIGS. 6 and 7, acting as illumination beam partitioning mechanism 50, segments the illumination beam to provide one or more light bearing partitions 150 separated by one or more non-light bearing partitions 152. Movement of reciprocating partitioning member 129 then scans the segmented illumination provided by light-bearing partitions across the area of pupil P. In the sequence of FIGS. 8A–8D, scanning is effected in the direction of the outlined arrow. Following this overall pattern, reciprocating partitioning member 129 partitions shaped illumination beam $I_{shaped}$ so that, at any instant, one or more light bearing partitions 150 or segments of the shaped illumination beam $I_{shaped}$ are directed into pupil P. These light bearing partitions 150 are then shifted in position to provide a scanning effect over the pupil that enables the complete image to be obtained over time.

Figure 9:
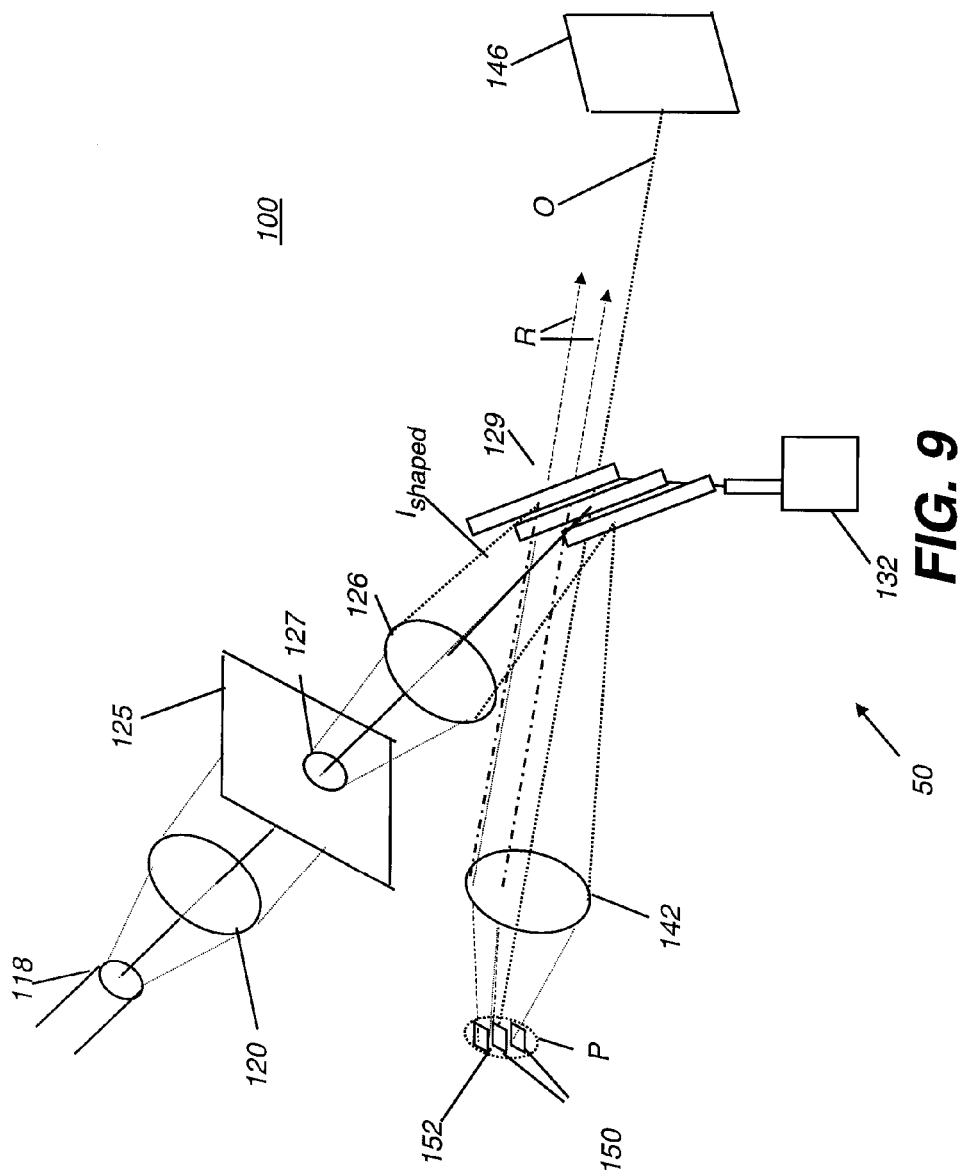
FIG. 9 is a perspective block diagram showing the beam partitioning behavior of the illumination apparatus of the present invention.

Referring to FIG. 9, the result of this partitioning behavior of reciprocating partitioning member 129 within fundus imaging apparatus 100 is shown for one embodiment. Reciprocating partitioning member 129 reflects shaped illumination beam $I_{shaped}$ from spatial light modulator 125 along optical axis O towards the pupil P (shown in dotted outline in FIG. 9), with this light segmented into a set of light bearing partitions 150 separated by non-light bearing partitions 152. Reflected light R from the eye then travels back along optical axis O. The unwanted reflected light from the cornea is substantially blocked by suitable portions of reciprocating partitioning member 129. The desired light from the retina is transmitted to sensor 146. To provide scanning action that allows a complete image to be obtained over time, an actuator 132 is coupled to reciprocating partitioning member 129 to provide reciprocating movement.

Figure 10:
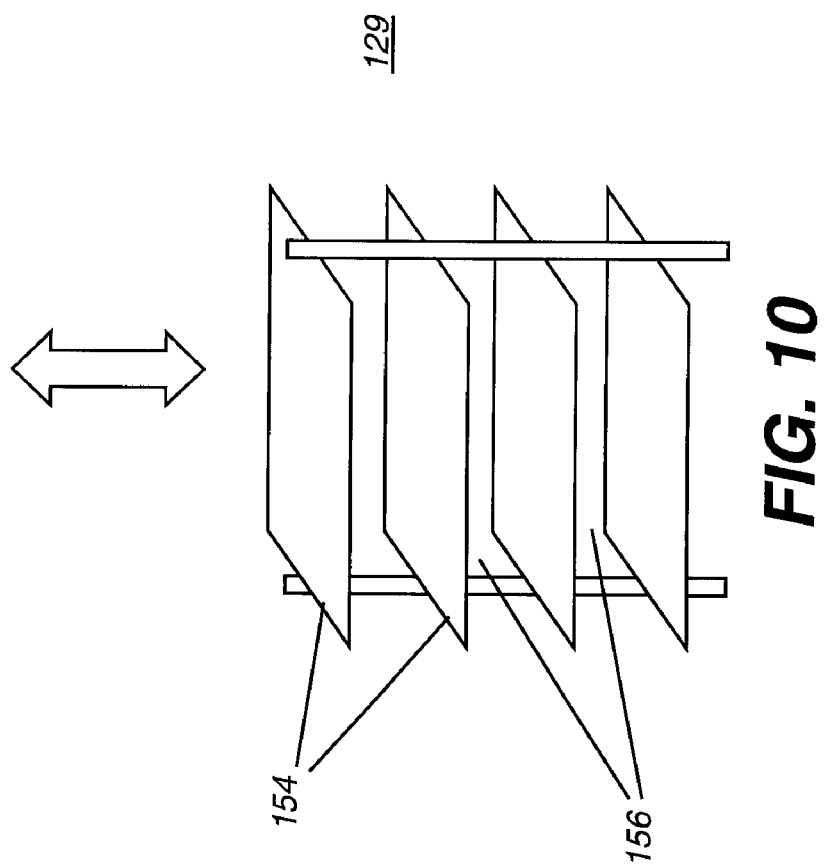
FIG. 10 is a perspective view showing a reciprocating partitioning member in one embodiment of the present invention.

One embodiment of reciprocating partitioning member 129 is shown in FIG. 10. One or more reflective members 154 reflects light into light bearing partitions 150. Gaps 156 between reflective members 154 correspond to non-light bearing partitions 152 of FIGS. 8A–8D, enabling the return of reflected light from the eye along the optical axis O to sensor 146. As the double-headed arrow in FIG. 10 indicates, reciprocating partitioning member 129 is moved up or down during scanning operation, in order to bathe the complete pupil P of eye E in light over time, using scanned light bearing partitions 150 to reflect the shaped illumination beam $I_{shaped}$ appropriately. The arrangement of reflective members 154 can have any number of alternate embodiments for partitioning the shaped illumination beam $I_{shaped}$. Reciprocating actuation, represented by actuator 132 in FIG. 9, can be provided by any number of electromechanical devices, including a solenoid, motor, piezoelectric actuator, pneumatic device, spring-loaded actuator, or other device. The speed of movement provided for this scanning effect can be varied, based on the response characteristics of sensor 146, the brightness of shaped illumination beam $I_{shaped}$, and other factors.

Figure 11:
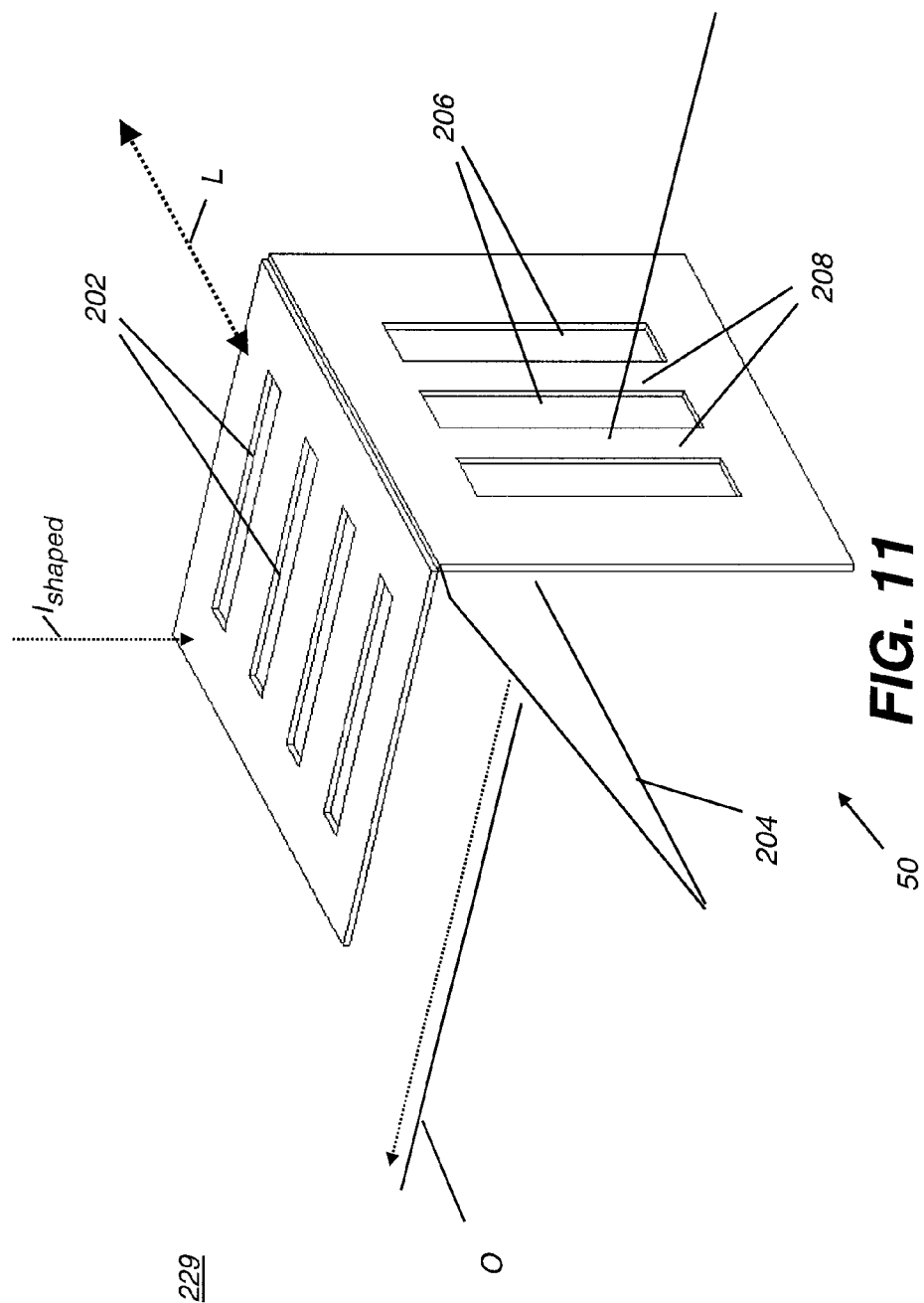
FIG. 11 is a perspective view showing an alternate reciprocating partitioning member in one embodiment of the present invention.

An alternate embodiment for partitioning the pupil as illumination beam partitioning mechanism 50 is shown in FIG. 11. Here, a reciprocating partitioning member 229, disposed within the path of shaped illumination beam $I_{shaped}$, has one or more slits 202 that provide an aperture for illumination. A beamsplitter 204 directs the partitioned illumination along optical axis O and toward the eye of the patient, following the general pattern of FIG. 6. Light reflected from the eye, returning along optical axis O, is directed by toward sensor 146 (FIG. 9) through apertures 206. One or more blocking members 208 block light reflected back from the corneal surface, so that the reflected light that goes to sensor 146 is from the retina. For scanning the complete pupil, linear movement is provided in the direction of arrow L in FIG. 11.

As the examples of FIGS. 10 and 11 clearly show, there can be a number of ways for implementing the overall function of illumination beam partitioning mechanism 50 performed by reciprocating partitioning member 129/229 of the present invention. This component partitions the shaped illumination beam $I_{shaped}$ into distinct light-bearing and non-light bearing partitions 150 and 152, scans light bearing and non-light bearing partitions 150 and 152 across the pupil to illuminate the full field over time, and blocks unwanted light that is reflected from the cornea.

Fundus Imaging Appliance 220

Figure 2:
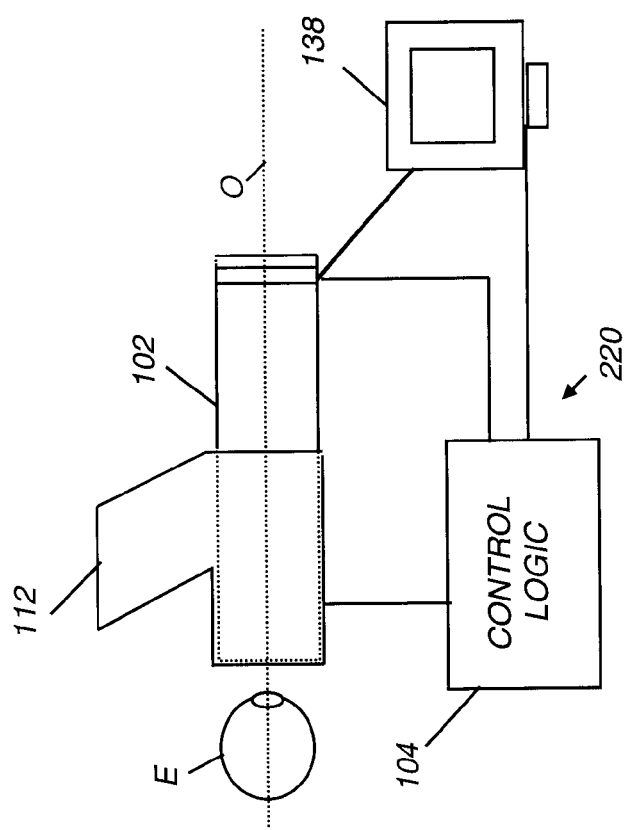
FIG. 2 is a schematic block diagram showing components of the imaging apparatus of the present invention.

Referring to FIG. 2, there is shown a schematic block diagram of key subsystems of fundus imaging appliance 220. The relative position of eye E is shown on an optical axis O. Alignment of illumination and imaging optics and delivery of light to the eye is performed by an illumination section 112. An image capture section 102 then cooperates with illumination section 112 components to obtain the retinal images from eye E. A control logic processor 104 within fundus imaging appliance 220 controls illumination section 112 and image capture section 102 components to maintain proper alignment relative to eye E and provide the optimal lighting characteristics for retinal imaging. Control logic processor 104 also executes pupil-tracking algorithms and provides signals for controlling imaging operation. Operator commands at control workstation 210 (FIG. 1) are provided to control logic processor 104 for manipulating component positioning, illumination, and imaging functions.

Figure 12:
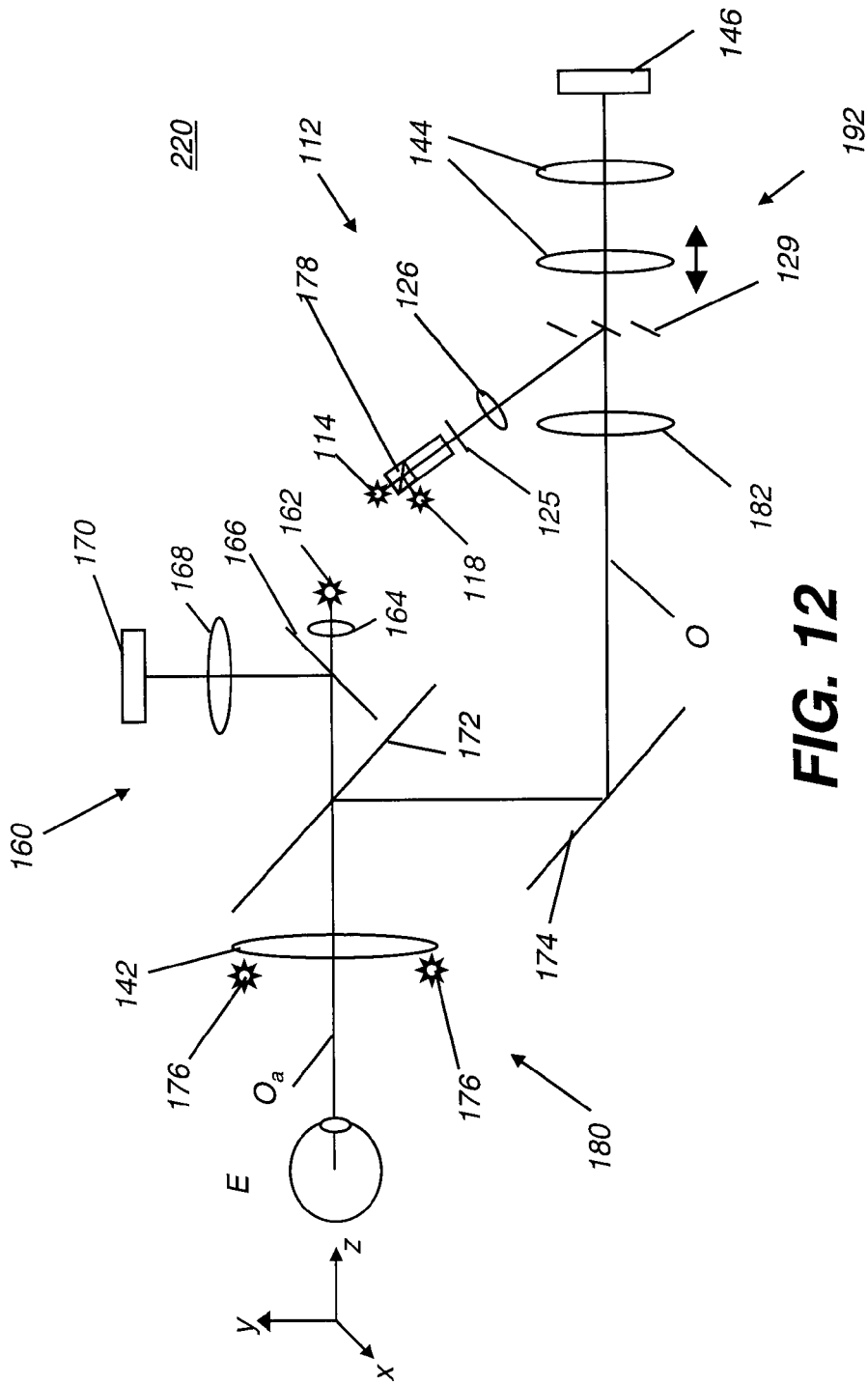
FIG. 12 is a block diagram of a fundus imaging apparatus in one embodiment.
Figure 13:
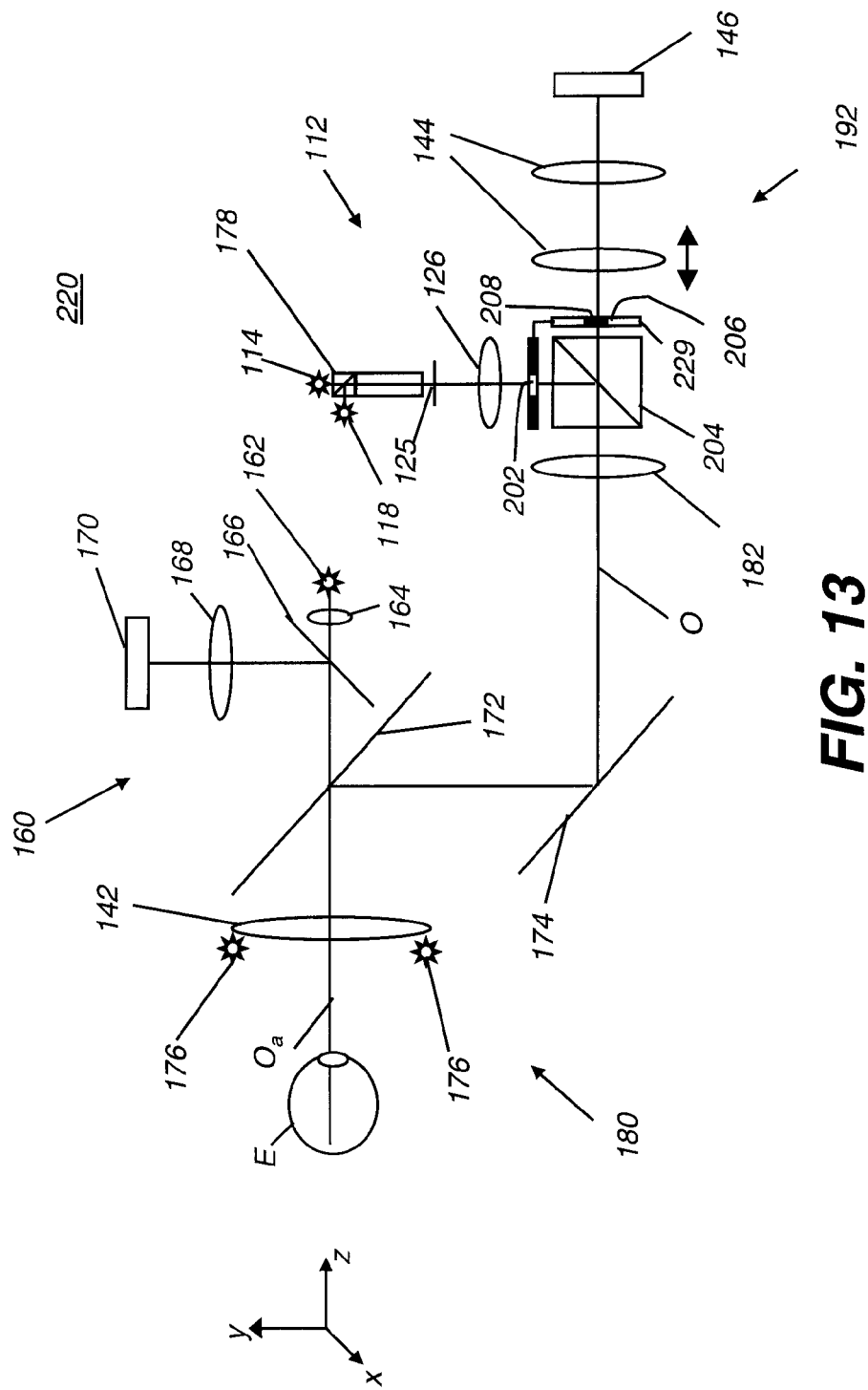
FIG. 13 is a block diagram of a fundus imaging apparatus in another embodiment.

Referring to FIG. 12, there is shown a block diagram of fundus imaging appliance 220 optical components in one embodiment of the present invention. In addition to illumination section 112 described above, fundus imaging appliance 220 has an alignment section 160, a cornea focusing section 180, and a retina focusing section 192. FIG. 13 shows an alternate embodiment of a fundus imaging appliance 220 using reciprocating partitioning member 229.

Figure 14:
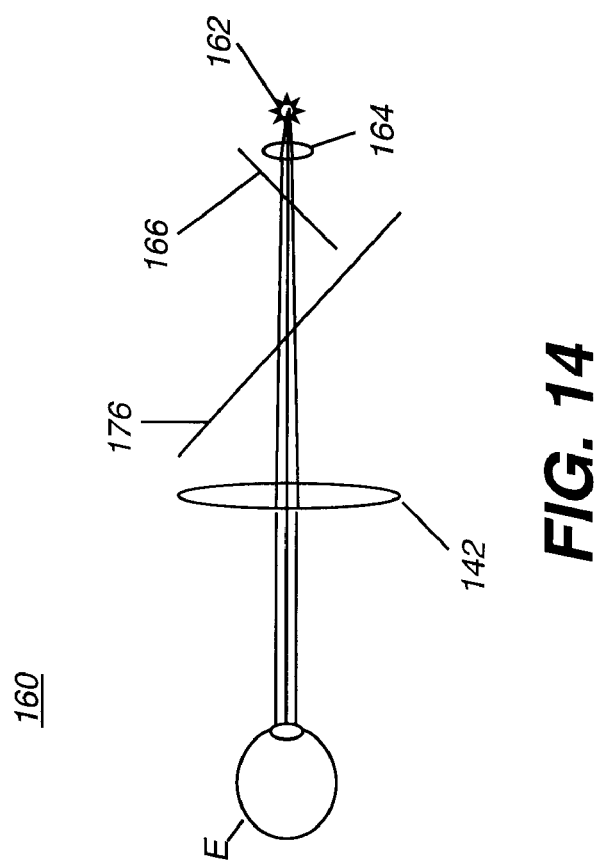
FIG. 14 is a block diagram of the alignment section of a fundus imaging apparatus.

Alignment section 160 provides aiming and accommodation of the patient's vision, in order to position the eye E favorably for fundus imaging. To simplify description, FIG. 14 isolates the basic components of alignment section 160 from the block diagrams of FIGS. 12 and 13. An aiming target 162, such as an LED or other light source, visible to the patient through beamsplitters 172 and 166, is used to direct the eye of the patient to a position that provides visual accommodation. That is, when viewing aiming target 162 through lens 142 and a lens assembly 164, the light entering eye E is substantially collimated. When the light entering eye E is collimated, light from illumination section 112 can be directed to the retina and more accurate focus adjustments can be made. Relative to the coordinate axes shown in FIG. 12, the alignment procedure along optical axis $O_a$ sets the position of eye E along the z axis, and provides alignment positioning relative to the orthogonal x and y axes.

FIGS. 12 and 13 also show different embodiments of illumination section 112 in more detail. A beamsplitter 178 in illumination section 112 directs light from either observation light source 114 or image capture light source 118 through spatial light modulator 125 and lens 126 for beam shaping and to reciprocating partitioning member 129 (FIG. 12) or 229 (FIG. 13) as illumination beam partitioning mechanism 50 for partitioning illumination to the pupil as was described generally with reference to FIGS. 8A–8D.

Lenses 182 and 142 direct the shaped and partitioned illumination beam into the pupil of eye E. Beamsplitters 172 and 174 fold optical axis O between lenses 182 and 142.

Figure 15:
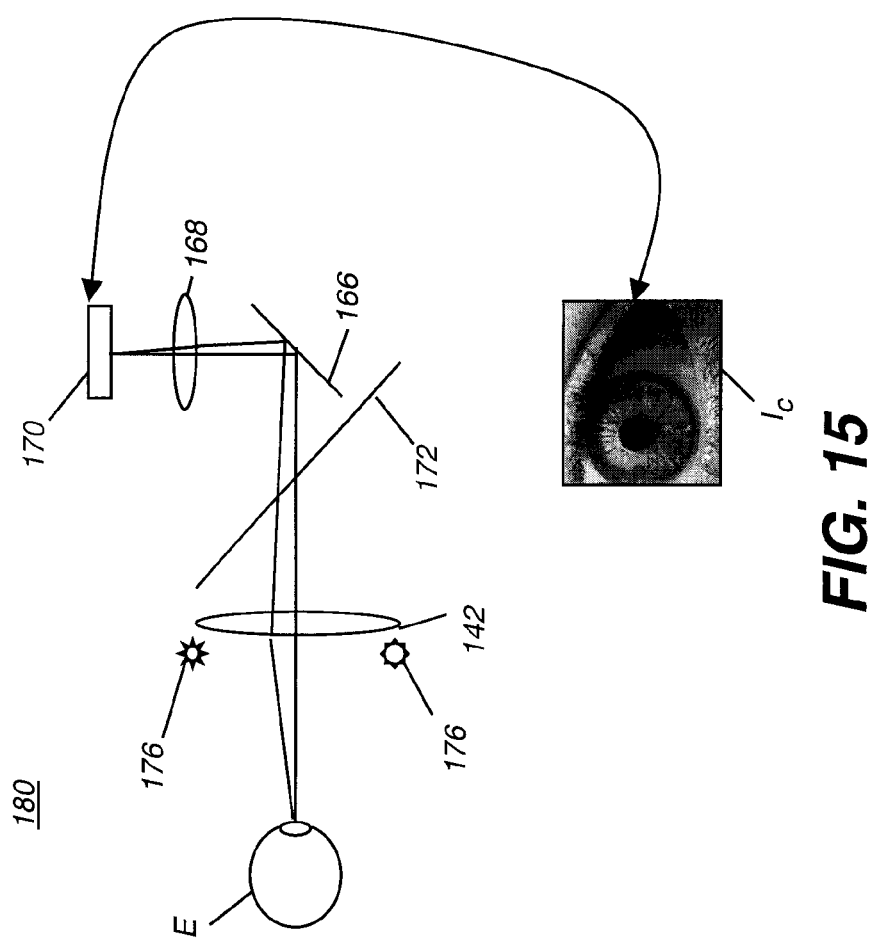
FIG. 15 is a block diagram of the cornea focusing section of a fundus imaging apparatus.

Once alignment of eye E is achieved, it is necessary to focus on the cornea using cornea focusing section 180. To simplify description, FIG. 15 isolates the basic components of cornea focusing section 180 from the block diagrams of FIGS. 12 and 13. With respect to FIG. 15, the purpose of cornea focusing section 180 is to adjust the focus of lens 142 or, with reference to FIGS. 12 and 13, to adjust for the position of the eye along the z-axis. When necessary to focus the cornea, pupil profiling light sources 176 provide peripheral illumination to the cornea. The reflected light is then directed, through beamsplitters 172 and 166 and through lens 168, to cornea camera 170, which is optically conjugate to the cornea. Cornea camera 170 can be a relatively inexpensive imaging device, requiring only that it have sufficient resolution for focusing. In one embodiment, for example, cornea camera 170 is a CCD camera, model no. IK-52V manufactured by Toshiba.

Figure 16:
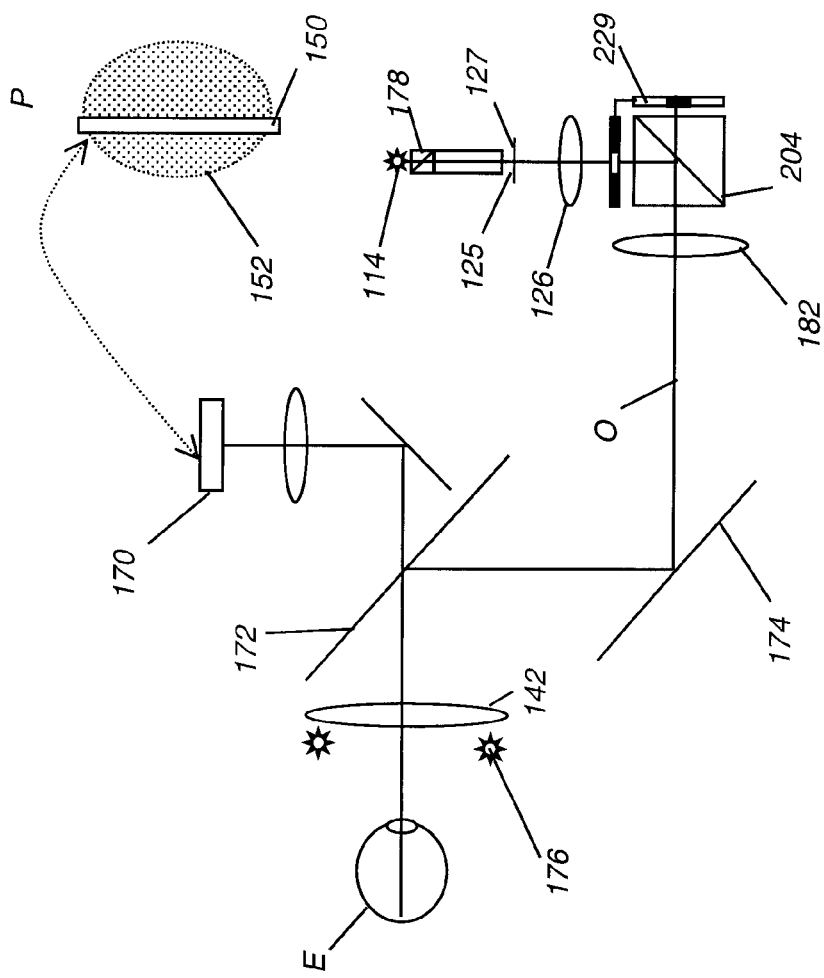
FIG. 16 is a block diagram of components used in preliminary retinal focusing.

Achieving proper focus through the cornea allows the retinal image to be obtained. As a first step, partitioned, shaped illumination beam $I_{shaped}$ is directed onto the cornea, imaging reciprocating partitioning member 129 or 229 onto the cornea. To simplify description for this step, FIG. 16 isolates the basic components used for this phase of retinal focus setup from the block diagrams of FIGS. 12 and 13. Observation light source 114 is conjugate with the cornea. For observation functions, an IR LED or similar source for observation light source 114 is directed through transmissive spatial light modulator 125 for beam shaping and through reciprocating partitioning member 229 and beamsplitter 204 for partitioning, then directed to the cornea of eye E along optical axis O. Cornea camera 170 detects the image of reciprocating partitioning member 229, which can be displayed on an accompanying CRT monitor (not shown) for example.

It must be observed that pupil profiling light sources 176, used for initial stages of cornea focus, are disabled during the step of cornea focus described with respect to FIG. 16. Light sources 176 are typically LEDs that emit IR light, or other non-visible light to which the iris is insensitive, so that the pupil dimensions are not effected by this light. Light of wavelengths used for pupil profiling light source 176 may alternately be visible, but should be in a range to which the eye is relatively insensitive. It must also be noted that similar behavior occurs whether reciprocating partitioning member 129 of FIG. 10 or reciprocating partitioning member 229 of FIG. 11 is used. Light bearing partitions 150 and non-light bearing partitions 152, once properly focused in this manner, can be scanned over the area of a pupil P to provide full retinal illumination.

Once the partitioned, shaped illumination beam $I_{shaped}$ is directed onto the cornea for observation, thereby forming an image of reciprocating partitioning member 129 or 229 onto the cornea, final adjustments can be made for sizing electronically controlled aperture 127 provided by transmissive spatial light modulator 125. In addition, any necessary final adjustments to retinal focus can be made. To simplify description for this step, FIG. 17 isolates the basic components used for final retinal focus from the block diagrams of FIGS. 12 and 13.

Figure 17:
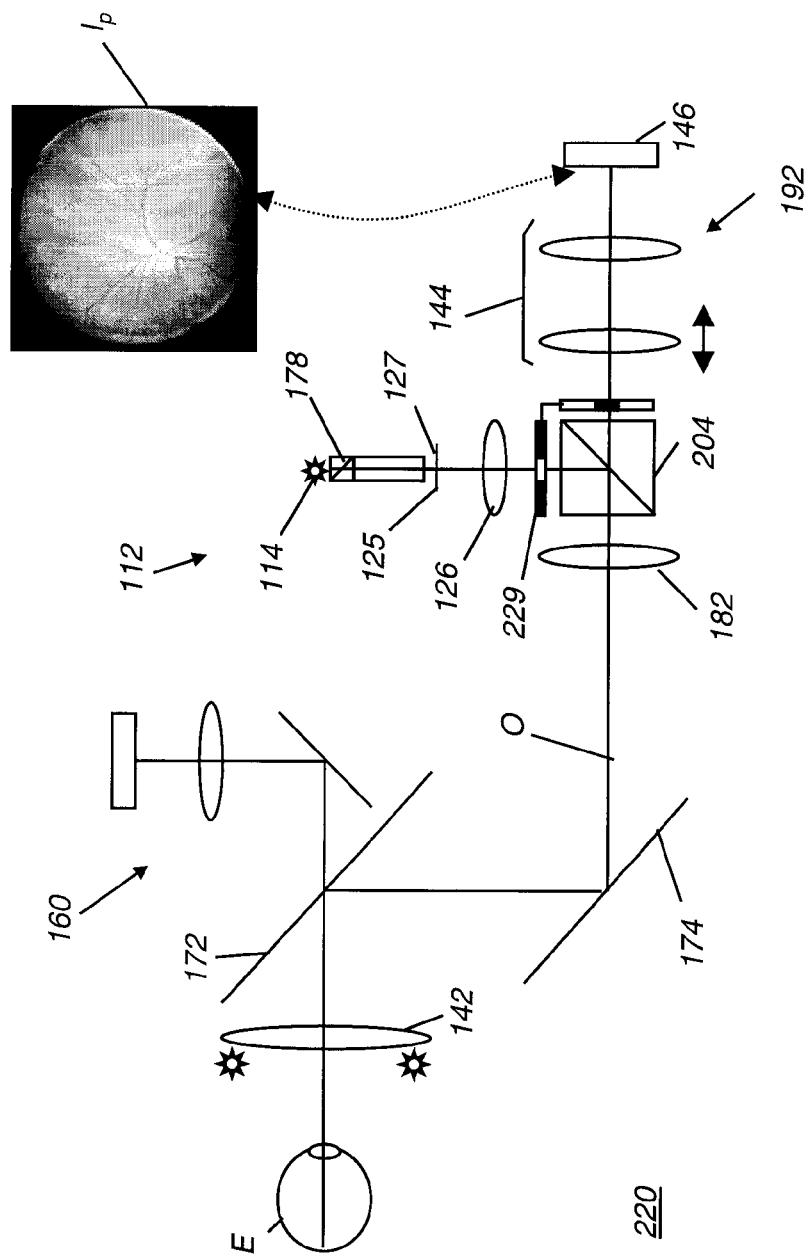
FIG. 17 is a block diagram of components used for preview and retinal focus.

Referring to FIG. 17, observation light source 114 provides illumination that is shaped and partitioned by illumination section 112, using either reciprocating partitioning member 129 or 229, for example. Lenses 182 and 142 cooperate to focus the partitioned, shaped illumination beam $I_{shaped}$ onto the cornea. The path of light reflected from the retina goes back through reciprocating partitioning member 129 or 229, which blocks at least a substantial portion of light reflected from the cornea. The retinal image is thereby made available, in scanned partition format, to sensor 146. A preview image $I_p$ is then displayed to the operator to enable focus adjustment of lens 144.

Figure 18:
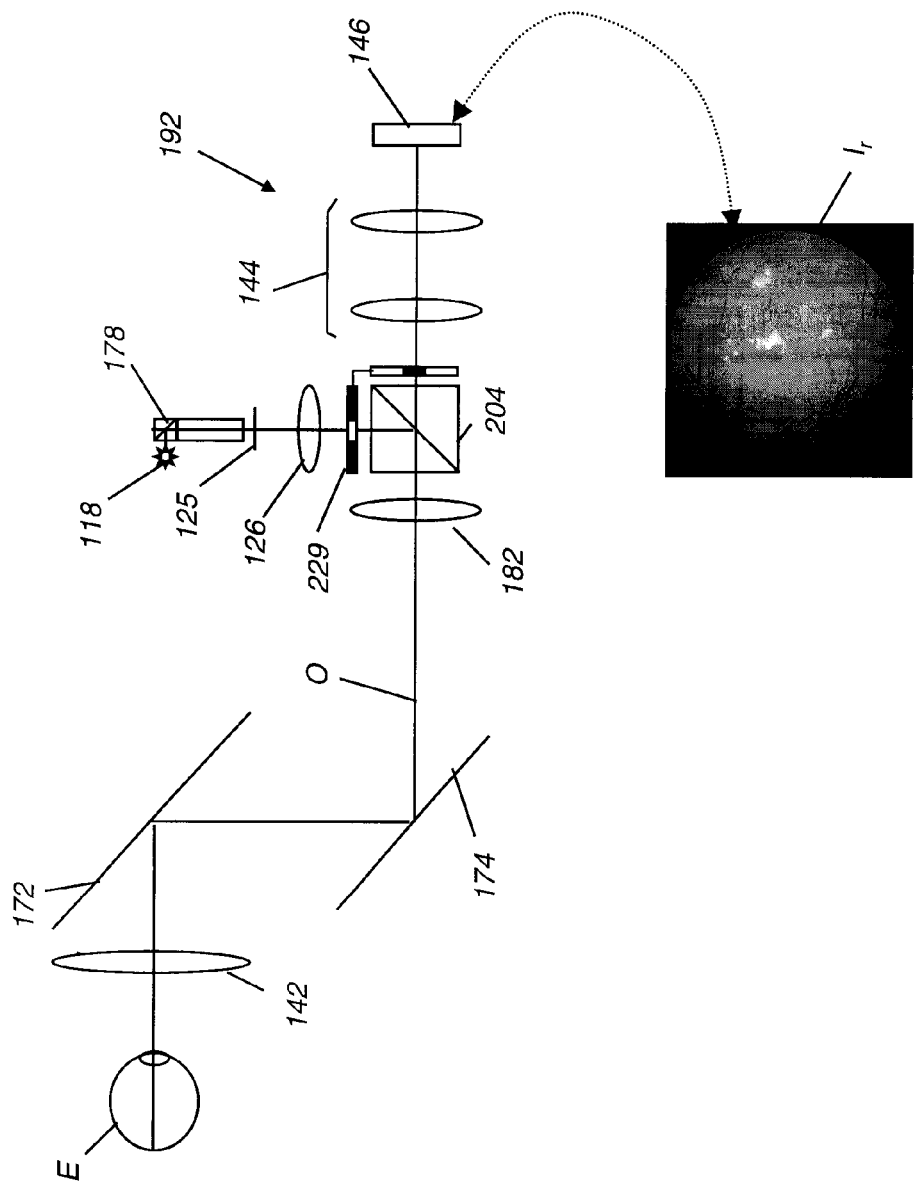
FIG. 18 is a block diagram of the imaging component path according to the present invention.

With the retina focused using preview image $I_p$, the retinal image can now be obtained. To simplify description for this step, FIG. 18 isolates the basic components used for retinal imaging from the block diagrams of FIGS. 12 and 13. Image capture light source 118, typically a visible light source, is now energized, producing a beam of illumination that is shaped and partitioned by illumination section 112, using either reciprocating partitioning member 129 or 229, for example. Lenses 182 and 142 cooperate to focus the partitioned, shaped illumination beam $I_{shaped}$ onto the cornea. As with the preview illumination described with reference to FIG. 17, the path of light reflected from the retina goes back through reciprocating partitioning member 129 or 229, which blocks at least a substantial portion of light reflected from the cornea. The retinal image is thereby made available, in scanned partition format, to sensor 146. A retina image $I_r$ is then displayed to the operator and can be stored electronically for transfer to some other location or for additional processing. Depending on the characteristics of light from image capture light source 118 and on sensor 146, the image obtained can be a multi-color image or a monochrome image.

During image capture, it may be useful to continually recheck eye E alignment as well as cornea and retinal focus. This type of continuous checking could be executed automatically or could be incorporated into operator procedures. For example, light sources 176 could be periodically energized to provide the operator with the opportunity for making any necessary focus readjustments. Pupil-tracking is described in more detail subsequently.

Component Arrangement of Fundus Imaging Appliance 220

Figure 20:
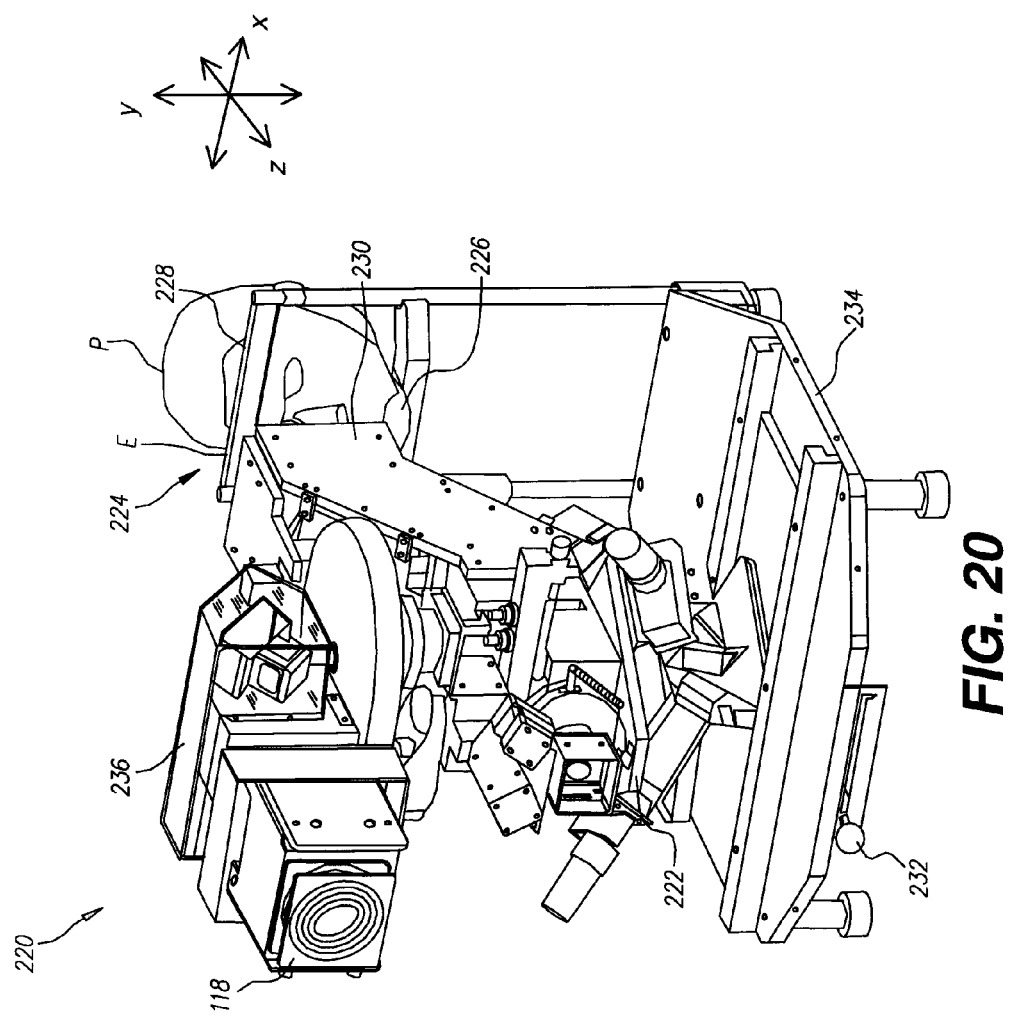
FIG. 20 is a perspective view showing component arrangement for the fundus imaging apparatus of the present invention.

Referring to FIG. 20, there is shown a perspective view of the component arrangement of fundus imaging appliance 220. Fundus imaging appliance 220 mounts fundus imaging system 100 on a translation stage 222 and a base 234. The patient P is positioned at an object position 224 that includes a chin rest 226 and forehead retainer 228, both acting as types of reference locators, helping to provide initial placement of the eye E (obstructed from view in FIG. 20) to be imaged. The patient looks through a view window 230. The operator uses a left/right selector 232 to position view window 230 near the eye to be imaged. Translation stage 222 is then used to move, as a body, the full set of imaging components that comprise fundus imaging appliance 220, thereby adjusting the XYZ positioning of view window 230.

Optical path components, as described hereinabove, systematically align eye E with the optical axis of imaging system components. Once the head of patient P is closely positioned with respect to viewing window 230, processing for this alignment begins. Then, once eye E alignment is achieved, a sequence is followed in which illumination is adapted for the pupil geometry of eye E and a retinal scan is obtained using this illumination. In the embodiment of FIG. 20, fundus imaging apparatus 220 includes an illumination housing 236 that provides support components that are suitably positioned for providing illumination of different types during alignment and focus and during image capture.

Alignment and Imaging Procedure

Figure 21:
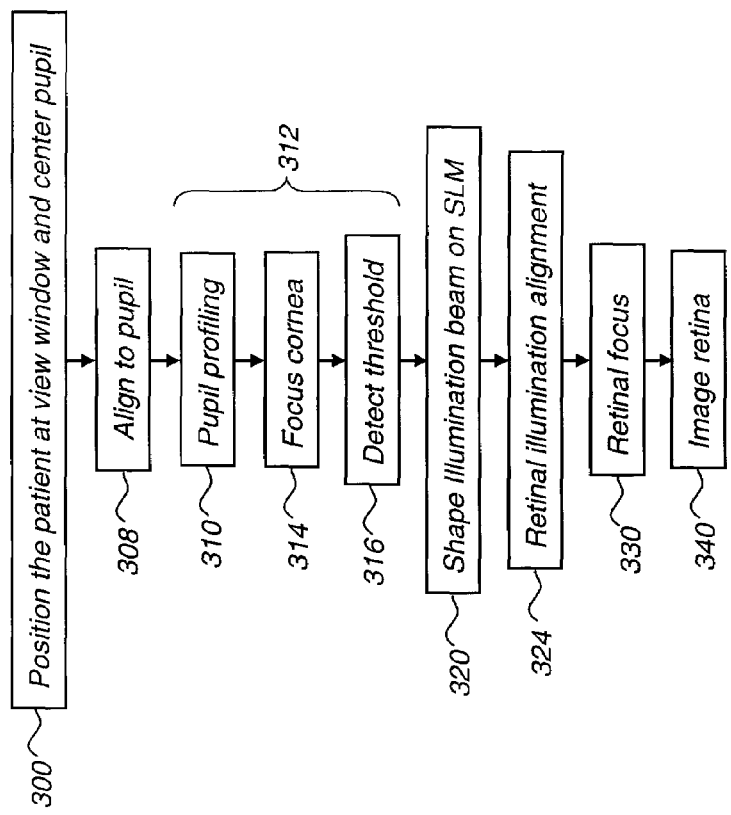
FIG. 21 is a process flow diagram showing the basic steps used for obtaining a retinal image using the imaging system of the present invention.

Fundus imaging appliance 220 provides an interface for operator action and control of the sequence for obtaining a retinal image. In one embodiment, the operator interface provides a guided sequence of steps that enable a relatively unskilled operator to successfully perform image capture. A combination of manual and automated procedures is used to help direct operator activity as well as to maintain proper adjustment of the system and proper alignment along the optical axis. Referring to FIG. 21, there is shown a process flow diagram that gives the basic sequence of steps for alignment and imaging. A number of these steps require operator interaction in one embodiment; however, it can be appreciated by those skilled in the instrumentation and imaging arts that many of the steps described using operator interaction can be automated, at least in part.

Figure 22A:
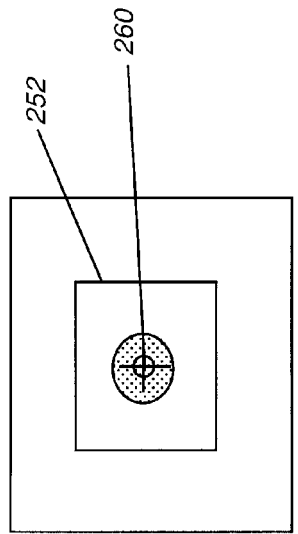
FIGS. 22A–22C are plan views showing an arrangement of operator interface display screens for the imaging system of the present invention.
Figure 22B:
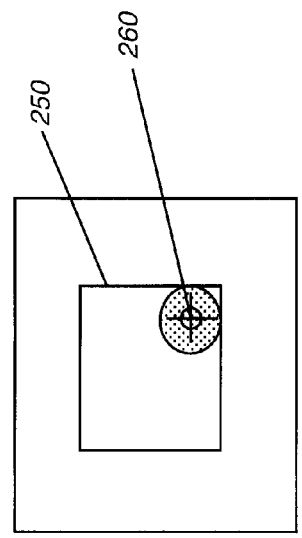

In a coarse positioning step 300, the patient is seated or otherwise comfortably accommodated at object position 224, as was described with reference to FIG. 20. Chin rest 226 can be adjusted for the patient. The operator adjusts the coarse horizontal position of viewing window 230 using left/right selector 232. Then, XYZ adjustment of viewing window 230 is performed. In one embodiment, a conventional computer mouse 213 (FIG. 1) is used to obtain a suitable XYZ position. Light source 176 is activated to illuminate the eye, giving the operator a reference for coarse positioning. On operator interface display 138, a thumbnail, black and white image 250 of eye E appears, as shown in FIG. 22A. The operator uses mouse 213, keyboard 212, touchpad, or other suitable pointing mechanism to manipulate the position of a cursor 260, centering it within the image of the pupil in image 250. On operator interface display 138, a monochrome image 250 of eye E appears, as shown in FIG. 22A. Motion control logic in fundus imaging appliance 220 responds by positioning translation stage 222 (FIG. 20) to align eye E with the optical axis of the apparatus. The operator can further "fine-tune" the alignment adjustment using any of various command entry tools to achieve a pupil-aligned image 252, as shown in FIG. 22B. With this procedure, the operator is ready to obtain suitable alignment of the pupil with respect to the optical axis.

In a pupil alignment step 308, a visual target, such as aiming target 162 (FIG. 12) is enabled, encouraging the patient to focus on the target, thereby providing visual accommodation so that the light entering the cornea of eye E is relatively well collimated. Initially, the target may be dim, because the optical axis O of fundus imaging apparatus 220 is not yet sufficiently aligned to the eye.

Once the operator is satisfied with pupil alignment, pupil profiling is executed, in which the outline and location of the pupil is determined. Pupil profiling, identified as the grouping of steps labeled 312 in FIG. 21, is also a component of ongoing pupil-tracking that continues during later steps, as described subsequently. In an initial pupil profiling setup step 310, pupil profiling light source 176 illuminates the cornea. In a related focus step 314, the operator adjusts the focus relative to the cornea of eye E. Focus adjustment can be manual or can be automated, accomplished by entry of commands at operator interface display 138. Once suitable focus is achieved, a threshold detection step 316 is executed by image analysis software in control logic processor 214. In this step, the image analysis software determines the peripheral outline of the pupil, using image thresholding algorithms and techniques well known in the image analysis arts. The operator has the option for adjusting the threshold sensitivity for achieving the optimal outline data.

Once the pupil outline is obtained by the pupil profiling steps outlined above, a beam-shaping step 320 is executed by control logic. This step determines the size, shape, and XY position of the illumination beam $I_{shaped}$ (FIG. 7) to be provided through the cornea of eye E. For the following steps, this shaped illumination beam is used for providing both preview image and the actual fundus image.

Figure 22C:
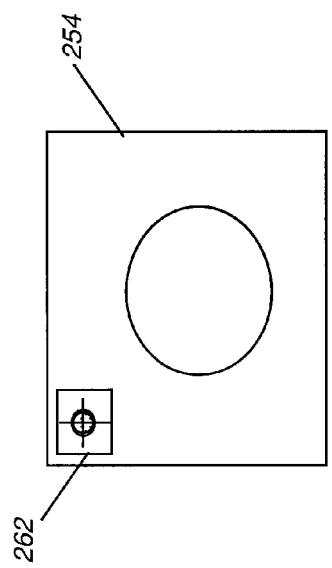

A retinal illumination alignment step 324 is then executed. During this step, both cornea and retinal illumination may be on simultaneously and pupil tracking may be temporarily disabled. Device optics remain focused on the cornea. Here, the diameter and XY position of the illumination beam $I_{shaped}$ (FIG. 7) are fine-tuned for imaging. Next, a retina focus step 330 is performed, using infrared illumination, to obtain final focus with respect to the retina. As shown in FIG. 22C, the corneal image now becomes a thumbnail image 262 and a full-size image 254 provides a monochrome preview image on display 138.

The preview function provides the operator with a number of options for checking adjustment, verifying image quality, and making needed readjustments. For example, as was noted in description of electronically controlled aperture 127 above, the operator may also control the relative intensity of light that is provided for imaging. Threshold adjustments allow the operator to condition the cross-sectional shape of the illumination beam appropriately under given conditions, adjusting electronically controlled aperture 127 appropriately. As described with reference to FIG. 17, observation light source 114 is energized for obtaining the preview image. The operator views the preview image and performs any needed focus adjustment for retinal imaging. Then, in an image capture step 340, the operator instructs fundus imaging apparatus 220 to obtain retinal images, using the components and sequence described hereinabove with reference to FIG. 18.

Pupil Tracking

During a number of the steps shown in FIG. 21 and outlined above, pupil tracking is performed. Pupil tracking helps to maintain suitable alignment of the eye and to compensate for slight head movements so that suitable illumination can be provided to the eye for accurate imaging. Referring back to FIG. 15, the optical path components of cornea focusing section 180 are used to provide pupil tracking during setup of fundus imaging appliance 220. Image data obtained from cornea camera 170, refreshed at a suitable rate for pupil tracking, is analyzed using any of a number of suitable algorithms for pupil tracking, such as any of the following, for example:

(i) center of mass calculation that determines the center of the pupil opening and uses a fixed or adjustable diameter as a pupil shape;

(ii) threshold evaluation that automatically determines a threshold source image value representing pupil area and uses that threshold to trace out the pupil outline; this method could alternately use a median filter for smoothing;

(iii) threshold evaluation combined with a connected components analysis that identifies the pixel area; or (iv) threshold evaluation that locates the center and bounding box of the pupil region.

Figure 23:
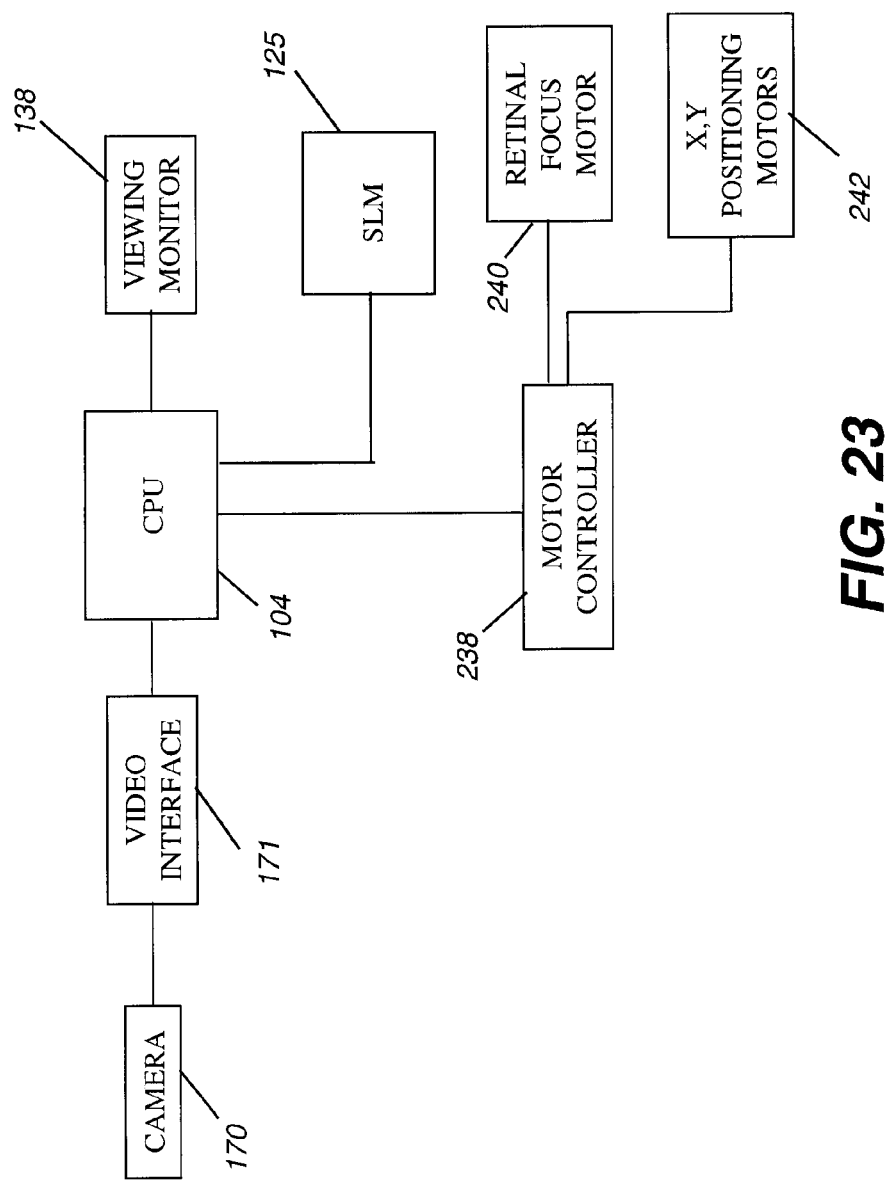
FIG. 23 is a schematic block diagram showing components used in pupil tracking.

In one embodiment, an automated arrangement of components in a control loop for maintaining pupil tracking is provided, as shown in FIG. 23. An image of the cornea is obtained from cornea camera 170 and processed through a video capture interface component 171. Control logic processor 104 provides an image for viewing on display 138 and computes, from the obtained data, any necessary changes to the position and shape of the illumination beam. For very small pupil movements, control logic processor 104 simply adjusts the illumination beam shape at spatial light modulator 125, thereby manipulating electronically controlled aperture 127, as described above. Alternately, if some repositioning of components is needed to accommodate a larger movement distance, control logic processor 104, in cooperation with a motor controller 238, drives a retinal focus motor 240, one or more XY positioning motors 242, or other actuator device.

As is shown in FIG. 22C, operator interface utilities provided to support ongoing adjustment checking include the use of a thumbnail image 262, periodically refreshed, that gives some indication of pupil alignment and focus. Thumbnail image 262 conveniently appears on the same screen with retinal image 254 in this embodiment.

Unlike conventional fundus imaging devices currently in use, the apparatus of the present invention is advantaged in its capability to provide full color fundus imaging. Corneal and preview images may be obtained inexpensively and efficiently using monochrome images, with full-color imaging used for the final retinal images.

The present invention provides a fundus imaging apparatus that is simple to operate, allows compact packaging, and does not require dilation of the pupil for most patients. It must be emphasized that fundus imaging appliance 220, as described in the present application, is primarily intended to provide basic fundus imaging that can be inexpensively performed at the office of a PCP or other non-specialist site. Thus, more advanced imaging features and functions are omitted from this description of fundus imaging system 100 and fundus imaging appliance 220. However, the same apparatus and methods used for illumination of the eye described hereinabove could also be applied to a more sophisticated imaging device. In particular, methods for scanning the retina with partitions of illumination may prove beneficial for other types of ophthalmic imaging devices.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, the various light sources used within fundus imaging appliance 220 allow a number of optional types. Sensors and CCD devices could be any of a number of different types. Although the resolution and overall image quality requirements for cornea camera 170 and sensor 146 are quite different, a single CCD array could be used for both cornea camera 170 and sensor 146, switched between these functions, using techniques well known in the imaging arts. Various types of reference locators could be used for assisting in the initial positioning of the patient. The patient is preferably seated; however, imaging could be obtained from a patient in some other position.

Within illumination beam partitioning mechanism 50, various types of actuators and mechanisms could be used for performing the functions of scanning reciprocating partitioning member 129/229. Possible actuator types include electromagnetic and piezoelectric actuators or acoustical transducers. Alternately, devices used could be spring-mounted. Other types of electromechanical actuators could be used.

There are numerous options for operator interface utilities and command entry devices. An optional keypad could be provided on fundus imaging apparatus and a display 138 built into the unit itself, such as a touchscreen for example, rather than being a separate component as is shown in the block diagram of FIG. 1.

Thus, what is provided is an apparatus and method for fundus imaging using scanned illumination.

PARTS LIST

- 10 fundus imaging apparatus
- 12 illumination section
- 14 observation light source
- 16 lens
- 18 image capture light source
- 20 lens
- 22 half-mirror
- 24 ring-slit diaphragm
- 26 lens
- 28 apertured mirror
- 30 inner ring
- 32 middle section
- 34 outer section
- 36 pupil
- 40 ring
- 42 lens
- 44 lens
- 46 sensor
- 50 illumination beam partitioning mechanism
- 100 fundus imaging system
- 102 image capture section
- 104 control logic processor
- 112 illumination section
- 114 observation light source
- 116 lens
- 118 image capture light source
- 120 lens
- 122 half-mirror
- 125 spatial light modulator
- 126 lens
- 127 electronically controlled aperture
- 129 reciprocating partitioning member
- 130 control logic processor
- 132 actuator
- 138 display
- 142 lens
- 144 lens
- 146 sensor
- 150 light bearing partition
- 153 non-light bearing partition
- 154 reflective member
- 156 gap
- 160 alignment section
- 162 aiming target
- 164 lens assembly
- 166 beamsplitter
- 168 lens
- 170 cornea camera
- 171 video capture interface
- 172 beamsplitter
- 174 beamsplitter
- 176 light source
- 178 beamsplitter
- 180 cornea focusing section
- 182 lens
- 184 mirror
- 186 uniformizer
- 188 prism 190 digital micromirror device
192 retina focusing section
202 slit
204 beamsplitter
206 aperture
208 blocking member
210 control workstation
212 keyboard
213 mouse
214 control logic processor
216 network
220 fundus imaging appliance
222 translation stage
224 object position
226 chin rest
228 forehead retainer
229 reciprocating partitioning member
230 view window
232 left/right selector
234 base
236 housing
238 motor controller
240 retinal focus motor
242 xy positioning motor
250 image
252 image
254 image
260 cursor
262 thumbnail image
300 coarse positioning step
308 pupil alignment step
310 pupil profiling setup step
312 pupil profiling step
314 focus step
316 threshold detection step
320 beam-shaping step
324 retinal illumination alignment step
330 retina focusing step
340 image capture step

The invention claimed is:

1. An apparatus for obtaining a scanned image of an eye, comprising:
   a) a reference locator for positioning a patient at a viewing position;
   b) a pupil alignment apparatus for aligning the pupil of the eye along an optical axis;
   c) a pupil profiling apparatus for obtaining an outline of the pupil using light outside the visible spectrum, comprising:
      i) a pupil profiling light source for illuminating the eye surface;
      ii) a sensor for detecting reflected light from the pupil profiling light source;
      iii) a control logic processor in communication with said sensor for computing an outline of the pupil according to detected light;
   d) an illumination apparatus for directing visible illumination into the eye, comprising:
      i) a spatial light modulator for shaping an illumination beam, in cross-section perpendicular to the beam direction, according to the detected outline of the pupil;
      ii) a scanning element for scanning at least one partition of the shaped illumination beam into the pupil; and
   e) a camera for obtaining the scanned image by sensing a portion of the illumination beam reflected from within the eye.

2. An apparatus according to claim 1 wherein the scanning element reciprocates between a plurality of positions.

3. An apparatus according to claim 1 wherein the scanning element further blocks a portion of the illumination beam reflected from within the eye.

4. An apparatus according to claim 1 further comprising a translation stage for adjusting the position of said pupil alignment apparatus, said pupil profiling apparatus, said illumination apparatus, and said camera.

5. An apparatus according to claim 1 wherein the spatial light modulator is a transmissive LCD.

6. An apparatus according to claim 1 wherein the spatial light modulator is a reflective LCD.

7. An apparatus according to claim 1 wherein the spatial light modulator is a digital micromirror device.

8. An apparatus according to claim 1 further comprising a display.

9. An apparatus according to claim 1 wherein the spatial light modulator forms an aperture for shaping the illumination beam.

10. An apparatus according to claim 1 wherein the spatial light modulator is adjustable for varying illumination beam intensity.

11. An apparatus according to claim 1 wherein the pupil profiling apparatus further comprises a pointing mechanism for operator identification of the pupil on a display.

12. An apparatus according to claim 1 wherein the pupil profiling light source uses infrared light.

13. An apparatus according to claim 1 wherein the pupil profiling light source uses light outside the visible spectrum.

14. An apparatus for obtaining a scanned image of the eye, comprising:
   a) an adjustable alignment section for aligning the pupil of the eye along an optical axis;
   b) a first light source for illuminating the eye surface;
   c) a sensor for detecting light from the first light source reflected from the eye and forming a first image of the eye surface;
   d) a display for displaying the first image to an operator;
   e) at least one pointing mechanism for providing a pupil-locating signal from the operator;
   f) a control logic processor for detecting an outline of the pupil according to the first image from the sensor;
   g) an illumination apparatus for shaping an illumination beam according to the detected outline of the pupil and for scanning a partition of the shaped illumination beam into the pupil; and
   h) a camera for obtaining the scanned image by sensing the illumination beam reflected from within the eye.

15. An apparatus according to claim 14 wherein the first light source is an infrared light source.

16. An apparatus according to claim 14 wherein the sensor comprises a camera.

17. An apparatus according to claim 14 wherein the display comprises a touchscreen.

18. An apparatus according to claim 14 wherein the at least one pointing mechanism is taken from the group consisting of a mouse, an electronic stylus, a keyboard entry, and a touchscreen.

19. An apparatus according to claim 14 further comprising a translation stage for moving the apparatus into position for a patient.

20. An apparatus according to claim 14 wherein the control logic enables a threshold adjustment for pupil outline detection.

21. An apparatus according to claim 14 wherein both the first image and the scanned image appear simultaneously on the display.

22. An apparatus according to claim 14 wherein the scanned image is a multi-color image.

23. An apparatus according to claim 14 wherein the illumination section comprises:
   i) a spatial light modulator for shaping the illumination beam by forming an electronic aperture; and
   ii) a light intensity control for adjusting data levels provided to at least one pixel modulator in the spatial light modulator.

24. An apparatus according to claim 23 wherein the spatial light modulator is a transmissive LCD.

25. An apparatus according to claim 23 wherein the spatial light modulator is a reflective LCD.

26. An apparatus according to claim 23 wherein the spatial light modulator is a digital micromirror device.

27. An apparatus according to claim 14 further comprising a network interface for transmitting the scanned image to a networked site.

28. An apparatus according to claim 27 wherein the network interface further serves for downloading logic control software to the apparatus.

29. An apparatus according to claim 27 wherein the network interface is wireless.

30. A method for obtaining a scanned image of an eye, comprising:
   a) positioning a patient at a viewing position using a reference locator;
   b) aligning the pupil of the eye along an optical axis;
   c) obtaining an outline of the pupil using light outside the visible spectrum, comprising the steps of:
      i) illuminating the eye surface using a first light source;
      ii) detecting the light of the first light source that is reflected from the eye;
      iii) computing an outline of the pupil according to the detected light of the first light source;
   d) directing visible illumination into the eye, comprising the steps of:
      i) shaping an illumination beam, in cross-section perpendicular to the beam direction, according to the detected outline of the pupil;
      ii) scanning at least one partition of the shaped illumination beam into the pupil; and
   e) obtaining the scanned image by sensing a portion of the illumination beam reflected from within the eye.

31. The method of claim 30 wherein the step of illuminating the eye surface using the first light source comprises the step of directing infrared light toward the eye.

32. The method of claim 30 wherein the step of obtaining an outline of the pupil further comprises the steps of
   a) displaying an image of the eye according to the reflected light of the first light source that is detected; and,
   b) receiving a signal from a pointing device for aligning the display relative to the pupil.

33. The method of claim 30 further comprising the step of tracking pupil movement after the outline of the pupil has been obtained.

34. A method for obtaining a scanned image of the eye, comprising:
   a) illuminating the eye surface from a first light source;
   b) detecting light from the first light source reflected from the eye and forming a first image of the eye surface from the detected light;
   c) displaying the first image to an operator;
   d) obtaining a pupil-locating signal from a pointing mechanism manipulated by the operator;
   e) aligning the pupil of the eye along an optical axis according to the pupil-locating signal;
   f) detecting an outline of the pupil from the detected light;
   g) shaping an illumination beam according to the detected outline of the pupil;
   h) scanning a partition of the shaped illumination beam into the pupil; and
   i) obtaining the scanned image by sensing the illumination beam reflected from within the eye.

35. A method according to claim 34 wherein the step of obtaining a pupil-locating signal comprises the step of obtaining data on the position of a cursor manipulated on a display by the operator.

36. A method according to claim 34 wherein the step of aligning the pupil along an optical axis comprises the step of activating an actuator.

37. A method according to claim 34 wherein the step of illuminating the eye surface from a first light source comprises the step of illuminating the eye from a non-visible light source.

* * * * *